(12) United States Patent
Tran et al.

(10) Patent No.: US 8,249,731 B2
(45) Date of Patent: Aug. 21, 2012

(54) SMART AIR VENTILATION SYSTEM

(76) Inventors: Alexander Bach Tran, Saratoga, CA (US); Alan An-Thuan Tran, Saratoga, CA (US); Bao Q. Tran, Saratoga, CA (US)

( * ) Notice: Subject to any disclaimer, the term of this patent is extended or adjusted under 35 U.S.C. 154(b) by 0 days.

(21) Appl. No.: 12/960,743

(22) Filed: Dec. 6, 2010

(65) Prior Publication Data
US 2011/0077758 A1 Mar. 31, 2011

Related U.S. Application Data

(63) Continuation-in-part of application No. 11/832,697, filed on Aug. 2, 2007, now Pat. No. 7,884,727, and a continuation-in-part of application No. 11/768,381, filed on Jun. 26, 2007, now abandoned.

(60) Provisional application No. 60/939,856, filed on May 24, 2007.

(51) Int. Cl.
*G06F 17/00* (2006.01)

(52) U.S. Cl. ............ 700/94; 340/572.1; 340/572.2; 340/572.3; 340/572.4; 340/539.1; 236/49.1; 236/49.2; 236/49.3; 236/49.4; 236/49.5; 222/23; 222/52; 222/69

(58) Field of Classification Search ......... 340/539.1, 340/572.1–572.5; 236/49.1–49.5; 222/23, 222/52, 69
See application file for complete search history.

(56) References Cited

U.S. PATENT DOCUMENTS

| | | | |
|---|---|---|---|
| 4,197,537 A | 4/1980 | Follen | |
| 4,229,811 A | 10/1980 | Salem | |
| 4,239,961 A | 12/1980 | Lasar | |
| 4,310,756 A | 1/1982 | Sick | |
| 4,382,291 A | 5/1983 | Nakauchi | |
| 4,384,280 A | 5/1983 | Haag | |
| 4,408,224 A | 10/1983 | Yoshida | |
| 4,499,564 A | 2/1985 | Sirai | |
| 4,514,625 A | 4/1985 | Heiland | |
| 4,639,902 A | 1/1987 | Leverance | |
| 4,722,266 A | 2/1988 | Deckert | |
| 4,942,348 A | 7/1990 | Nilssen | |
| 4,952,911 A | 8/1990 | D'Ambrosia | |
| 5,086,385 A * | 2/1992 | Launey et al. | 700/83 |
| 5,150,099 A | 9/1992 | Lienau | |
| 5,240,487 A | 8/1993 | Kung | |
| 5,364,304 A | 11/1994 | Hampton | |
| 5,934,362 A * | 8/1999 | Barker, II | 165/48.1 |
| 5,966,090 A | 10/1999 | McEwan | |
| 5,986,600 A | 11/1999 | McEwan | |
| 6,026,987 A * | 2/2000 | Burnett et al. | 222/78 |
| 7,009,519 B2 * | 3/2006 | Leonard et al. | 340/572.8 |
| 2002/0120184 A1 | 8/2002 | Beck | |

(Continued)

OTHER PUBLICATIONS

Dietz, et al "Very Low Cost Sensing and Communication Using Bidirectional LEDs", MERL 2003.

*Primary Examiner* — George Bugg
*Assistant Examiner* — Ojiako Nwugo
(74) *Attorney, Agent, or Firm* — Tran & Associates

(57) ABSTRACT

A system to control energy consumption in a building having a plurality of rooms with a wireless data transceiver; an occupancy sensor; a temperature sensor; a processor coupled to the wireless data transceiver, the occupancy sensor and the temperature sensor; and an air register including a motor coupled to the processor, the motor opening or closing one or more air vents in response to sensed motion or room temperature.

19 Claims, 13 Drawing Sheets

U.S. PATENT DOCUMENTS

| | | | |
|---|---|---|---|
| 2004/0095237 A1* | 5/2004 | Chen et al. | 340/506 |
| 2004/0223891 A1* | 11/2004 | Brown | 422/124 |
| 2005/0055568 A1* | 3/2005 | Agrawala et al. | 713/200 |
| 2005/0143667 A1 | 6/2005 | Park | |
| 2005/0185575 A1 | 8/2005 | Hansen | |
| 2005/0240758 A1* | 10/2005 | Lord et al. | 713/153 |
| 2006/0028997 A1* | 2/2006 | McFarland | 370/252 |
| 2006/0132303 A1* | 6/2006 | Stilp | 340/539.22 |
| 2006/0291575 A1* | 12/2006 | Berkman et al. | 375/257 |
| 2007/0236946 A1* | 10/2007 | Petrakis et al. | 362/374 |
| 2007/0271006 A1* | 11/2007 | Golden et al. | 700/295 |
| 2008/0003938 A1* | 1/2008 | Baruschke et al. | 454/143 |
| 2008/0055108 A1 | 3/2008 | Han et al. | |
| 2009/0187499 A1 | 7/2009 | Mulder et al. | |
| 2009/0216528 A1* | 8/2009 | Gemello et al. | 704/232 |
| 2010/0012737 A1* | 1/2010 | Kates | 236/49.3 |
| 2010/0146712 A1 | 6/2010 | Finch et al. | |
| 2010/0243754 A1* | 9/2010 | Harris | 239/34 |
| 2011/0025497 A1* | 2/2011 | Zaveruha et al. | 340/540 |

* cited by examiner

SMART AIR VENTILATION SYSTEM

This invention is a continuation in part of application Ser. No. 11/832,697 filed Aug. 2, 2007 now U.S. Pat. No. 7,884,727 and Ser. No. 11/768,381, filed Jun. 26, 2007 now abandoned which claims priority from Provisional Application Ser. No. 60/939,856, filed May 24, 2007, the contents of which are incorporated by reference.

BACKGROUND

This invention relates generally to methods and systems for an air ventilation system.

Many building owners, including the owners of apartments, offices and hotels, continue to seek methods to decrease their heating, ventilating and cooling ("HVAC") expenses. One method to do so is to select minimum and maximum setback temperatures for a room when the room is not occupied. Motion detection devices have been used to determine if the room is occupied and thus being used. Motion detectors have also been used as intrusion detection devices, or surveillance systems, have been developed to monitor an area or space, to protect against the entry of unauthorized personnel into that area or space, and to provide an alarm signal when such entry occurs.

Motion sensors can be based on sonic or ultrasonic/acoustical detectors, photoelectric break-beam devices, passive infrared detectors, video systems, and radar or microwave-based systems. The sonic, ultrasonic or acoustical devices are illustrated in U.S. Pat. Nos. 4,499,564, 4,382,291, 4,229,811 and 4,639,902. In the devices disclosed in these patents the intrusion detection systems utilize an acoustical signal, either sonic or ultrasonic, which is transmitted into the space to be protected. The acoustical signal is reflected off of objects in the space or the walls forming the perimeter of the space and is collected by an acoustical receiver. The return signal represents the total reflected energy pattern for that space. A change in the signal received indicates some change in the space protected; however, these systems do not provide any means of identifying where, either directionally or distance-wise, in the protected space that the change has occurred. Thus, the only information derivable from such systems is whether or not such a change has occurred which then requires some form of follow-up by the security force. An additional limitation of systems of this type is that they are generally unacceptable in anything but a closed environment since they are subject to false alarms from naturally occurring sound changes such as generated by wind, thunder, or other naturally occurring sounds in an open environment.

The photoelectric break-beam devices are illustrated in U.S. Pat. Nos. 3,875,403, 4,239,961, 4,310,756, 4,384,280 and 4,514,625. In the devices disclosed, the intrusion detection system uses an active photo-beam projected into the area under surveillance. A detector sees the continuous beam at the opposite end of the detection zone. If the photo-beam is broken by an intruder, then an alarm is sounded. This type of system does not give any information above the distance of the intruder from the detector device. This system also requires two head units with the protection zone between them. This leads to a more complex installation than if only one unit is required.

Passive infrared detection technology is illustrated in U.S. Pat. Nos. 3,476,946, 3,476,947, 3,476,948 and 3,475,608. With systems such as these, changes in the infrared content of the light received by the device from the area under control is monitored and an alarm signal is generated if the infrared content changes. This is based on the presumption that the infrared content of the light will be affected by intruders, particularly individuals, entering into the controlled space. However, it has been found that such infrared detectors are falsely triggered by normal changes in the infrared content of the light in a space due to ordinary changes in the sun as well as the effects of clouds passing over the sun. Still further, such systems do not provide distance or direction information and thus require follow-up by security staff to determine the true nature of the cause that triggered the alarm.

The video based intrusion detection systems utilize a video camera to view an area under protection and are illustrated in U.S. Pat. Nos. 3,823,261; 3,932,703 and 4,408,224. Typically, the video signal is digitized and stored in a memory. Thereafter, the video signal is compared with a reference signal stored in the memory and, when a difference is detected, an alarm is sounded. These systems use changes in scene illumination to determine an alarm condition rather than changes in object distances and therefore, unless the space to be observed and protected is carefully controlled and isolated from changes in environmental illumination, such changes will result in false alarms. As a result, such a system is less than satisfactory for exterior spaces. Furthermore, the amount of data that is necessarily stored to obtain reasonable resolution of the image of the space being protected requires a significant quantity of expensive computer memory.

Systems employing radar or other microwave technology are illustrated in U.S. Pat. No. 4,197,537. In this particular system a single microwave signal source is used to bathe the space with microwave energy. A receiver detects the return signal reflected from the space being protected which can be compared with a reference signal to detect an intrusion thereinto. This particular system is unable to identify the precise location of the intruder.

While other radar/microwave-based systems can provide such information, their cost can be significant. U.S. Pat. No. 4,952,911 discloses a scanning intrusion detection device that is capable of monitoring a large volume of either interior or exterior space from a single relatively inexpensive unit. This intrusion detection device has a radiation emitter arranged to scan a beam of infrared radiation about a field of view and means for receiving the radiation of the beam reflected from the field of view. The receiver is arranged to generate a signal indicative of the distance from the device at which the beam has been reflected for each of a plurality of azimuthal sectors of the field of view during a selected time period. The device stores a plurality of reference signals which are indicative of the distance of reflection of the beam from each azimuthal sector of the field of view during a reference time period. The signals from a selected time period are compared with the reference signals and an output signal is generated if one of the signals is different from the respective reference signal.

In a home, a central thermostat tells the heating or cooling system to turn on. Hot or cool air is pumped throughout the home until the central thermostat reaches the temperature you have selected. However, homes are composed of large and small rooms each with different windows, ductwork, and environments. Achieving a desired temperature in one room may cause another room to be over-heated or overcooled. Further, these systems do not automatically close air vents for rooms that are unused to conserve energy.

SUMMARY

In one aspect, a system to control energy consumption in a building having a plurality of rooms with a wireless data transceiver; an occupancy sensor; a temperature sensor; a processor coupled to the wireless data transceiver, the occupancy sensor and the temperature sensor; and an air register including a motor coupled to the processor, the motor opening or closing one or more air vents in response to sensed motion or room temperature.

Implementations of the above aspect may include one or more of the following. The air register is closed when the room is empty. A smart meter includes bi-directional communication, power measurement and management capability, software-controllable disconnect switch, and communication over low voltage power line. A thermostat can set room temperature. The thermostat wirelessly communicates with the data transceiver. The processor communicates with an online weather service for predicted weather condition. The processor pre-charges room temperature in response to a demand response signal or a predetermined pattern. The processor minimizes operating cost by shifting energy use to an off-peak period in response to utility pricing that varies energy cost by time of day. An energy harvester can power the system. The energy harvester can be a solar cell or a piezoelectric device that captures vibrational energy. A heating ventilation air conditioning (HVAC) device can be driven by a rechargeable energy reservoir, wherein the reservoir is charged during a utility off-peak period and used to power the HVAC device during a utility peak pricing period. A voice recognizer can be used to interpret user commands, such as a Hidden Markov Model (HMM) recognizer, a dynamic time warp (DTW) recognizer, a neural network, a fuzzy logic engine, a Bayesian network. The occupancy sensor can include an analyzer to process an RSSI signal from the wireless data transceiver to detect occupancy in the area. A light emitting diode can be used to detect light, wherein the processor determines lighting profiles that incorporate time-based control with occupancy, daylighting, and manual control and wherein the processor integrates time-based lighting control with occupancy sensing control. A heater, cooler, fan can be placed proximal to the air vent. A filter can be used to remove smoke contaminants from the air. One or more scent chemical reservoirs can deliver predetermined fragrance to the air filter. In another embodiment, the chemicals can be used with a stereo system and a display to provide an immersive virtual reality experience. For example, the virtual reality can be an ocean environment where the display shows gentle ocean waves, the stereo can play ocean sounds, and the fan/chemical reservoirs can deliver an ocean breeze sensation.

In another aspect, a system to control energy consumption in a room uses a wireless mesh network that allows for continuous connections and reconfiguration around blocked paths by hopping from node to node until a connection can be established, the mesh network including one or more wireless area network transceivers adapted to communicate data with the wireless mesh network, the transceiver detecting motion by analyzing reflected wireless signal strength.

In yet another aspect, an occupancy sensing system for an area includes one or more wireless nodes forming a wireless mesh network; and wireless transceiver adapted to communicate with the one or more wireless nodes, the wireless transceiver generating a received signal strength indication (RSSI) signal, wireless transceiver including an analyzer to process the RSSI signal to detect occupancy in the area.

In yet another aspect, a system includes a processor; a transceiver coupled to the processor and communicating an RSSI signal to indicate the presence of one or more persons in a room; and a light emitting diode (LED) coupled to the processor, the LED generating light in a first mode and sensing room light in a second mode.

Implementations of the above system may include one or more of the following. An appliance can be controlled by the transceiver, the appliance being activated or deactivated in response to sensed motion in the room based on the reflected wireless signal strength. A recognizer can be embedded in the transceiver including one of: a Hidden Markov Model (HMM) recognizer, a dynamic time warp (DTW) recognizer, a neural network, a fuzzy logic engine, a Bayesian network. The recognizer monitors one or more personally identifiable signatures. The transceiver identifies one person from another based on a Doppler heart rate signature. A sound transducer can be connected with the wireless transceiver to communicate audio over a telephone network through the mesh network. A call center or a receptionist or a person in a company's facility department can be connected to the transceiver to provide a human response such as a voice response to a question, or the call center can remotely turn off the appliance if appropriate. An in-door positioning system can be connected to one or more mesh network appliances to provide location information. The transceiver can be a Doppler radar. A wireless router can be connected to the mesh network and wherein the wireless router comprises one of: 802.11 router, 802.16 router, WiFi router, WiMAX router, Bluetooth router, x10 router. The transceiver can be a Multiple Input Multiple Output (MIMO) transceiver coupled to a plurality of MIMO antennas. The MIMO transceiver can operate as a Doppler radar. The transceiver transmits a pattern of predetermined varying burst widths and determines motion based on the received pattern of predetermined varied burst widths. A smart meter can control or communicate with the appliance. The smart meter includes bi-directional communication, power measurement and management capability, software-controllable disconnect switch, and communication over low voltage power line. A remote processor such as a processor in a different room or a different building can remotely turn power on or off for the appliance, read usage information from the meter, detect a service outage, detect the unauthorized use of electricity, change the maximum amount of electricity that the appliance can demand, and remotely change the meters billing plan from credit to prepay as well as from flat-rate to multi-tariff. The appliance minimizes operating cost by shifting energy use to an off-peak period in response to utility pricing that varies energy cost by time of day. A rechargeable energy reservoir can provide power to the appliance, wherein the reservoir is charged during a utility off-peak period and used during a utility peak pricing period. The appliance's operation is customized to each individual's preference. The appliance's operation can be customized to a plurality of individuals in a room by clusterizing all preferences and determining a best fit preference from all preferences. The mesh network can store and analyze personal information including one of: heart rate, respiration rate, medicine taking habits, eating and drinking habits, sleeping habits, excise habits. In a Doppler radar embodiment, the frequency of a radio signal is altered when the signal reflects off of a moving object. In one embodiment, the movement of people is detected. In another embodiment, the periodic movement of the chest and internal organs of the person modulates an incident or transmitted radio signal from one of the wireless transceivers, and the resulting reflection is interpreted to deduce, for example, heart and breathing activity. Transceivers that operate at high frequencies can be used to provide higher resolution and improved antenna patterns could be used for more detailed observations of arterial motion.

In other implementations, a light emitting diode (LED) can be connected to the wireless transceiver, the LED having a first mode to generate light and a second mode to generate a voltage based on ambient light. An analog to digital (ADC)

converter such as a sigma delta converter can read an output from the LED corresponding to ambient light in the area. The analyzer identifies one occupant from another based on a Doppler signature. The mesh network communicates lighting profiles that incorporate time-based control with occupancy, day-lighting, and manual control and wherein the analyzer integrates time-based lighting control with occupancy sensing control. The LED can sense sound in a third mode. The processor integrates time-based lighting control, sound detection control and occupancy sensing control.

Advantages of preferred embodiments of the system may include one or more of the following. The systems automatically close air vents for rooms that are unused to conserve energy. The system manages the climate of individual rooms in the home or office with ease. The system signals the vent to close when there is no occupant or when the desired temperature is reached. When the room is occupied, the system opens the vents to allow additional heating or cooling. The system automatically zones the home, allowing the user to set the desired temperature in a room and automatically have the vent shut when the temperature is reached or when the room is empty.

In addition to comfort, the system redistributes hot or cold air to other rooms allowing the home to reach its set temperature in a more efficient manner—reducing utility bills. With the vent automatically closed at the desired temperature or when the room is unoccupied, the heating or cooling that would have been wasted in one room is automatically redirected to the remaining rooms in the home.

In one implementation, the system provides motion sensing practically for free by simply adding software to each wireless transceiver and avoids extra hardware such as PIRs or photocells to detect people in a room, among others. The same wireless transceiver for controlling the appliance is used to sense motion and thus the cost is virtually free.

Other advantages may include one or more of the following. The system provides links between information technologies and electricity delivery that give industrial, commercial and residential consumers greater control over when and how their energy is delivered and used. The system provides wireless metering capability measurable to each device or appliance. Additionally, real-time electricity pricing information is used to optimize cost. The system links devices starting with the utility meter and reaches thermostats, household appliances, HVAC, pool pumps, water heaters, lighting systems and other household or building systems that are part of the home area network (HAN). The system provides a standards based approach to energy efficiency programs such as demand response, time-of-use pricing programs, energy monitoring, pay-as-you-use and net metering programs, enabling home owners use of distributed generation products like solar panels. These new energy management capabilities directly impact consumers and businesses as utilities grapple with meeting growing power demand while reducing the threat of rolling blackouts during peak usage periods. With the system, users can: view and react to energy consumption every day; track and adjust energy consumption; plan, budget and pre-pay their utilities bills; save energy and money based on price fluctuations; enhance conservation by using less energy during peak demands; and help the environment by helping consumers reduce greenhouse gas emissions through less energy usage. Thus, the system can save on HVAC costs, which can be 30-50% of a building's energy use.

The system can also save on lighting costs. Lighting commercial buildings in the United States currently consumes about 3.7 quadrillion Btus (British thermal units) of primary energy a year, equivalent to the output of over 175 modern power plants. Lighting accounts for 30 to 50% of a building's energy use, or about 17% of total annual US electricity consumption. Simply turning off unneeded lights can reduce direct lighting energy consumption up to 45%. Reducing lighting electricity usage reduces energy cost and lessens the environmental impacts associated with electricity generation. The system enables buildings to automatically dim electric lights in daylit spaces, and building occupants could manually dim local lighting according to preference, the U.S. energy savings could amount to more than half a quadrillion Btus per year—about 14 percent of annual energy use for lighting in commercial buildings.

Other advantages of RF wireless control include reduced capital and operating expenses. Wireless control can save as much as 30 to 40 percent on installation and material costs compared to a wired control system, making this option potentially attractive for retrofit as well as new construction. Maintenance expenses can be reduced because devices can be replaced one to one without control wiring being involved. As another potential benefit, RF wireless control offers flexibility centered on the mobility of devices, which can be moved and grouped based on evolving application needs without changing wiring. Wireless control systems are scalable, as devices can be added and removed easily. Based on adoption of open protocols, lighting control systems can be more easily integrated with other building systems such as HVAC and security. Intelligence can be both centralized and decentralized, with devices receiving commands from a central computer (and sending information back in a two-way stream), while also interacting with each other independently and allowing occupant control of local systems without location restraints. With wireless components, the system can grow over time and be reconfigured if needed at a much lower cost for a hard-wired system.

BRIEF DESCRIPTION OF THE DRAWINGS

FIG. 15A shows an exemplary air vent with filter, while

DESCRIPTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

Figure 1:
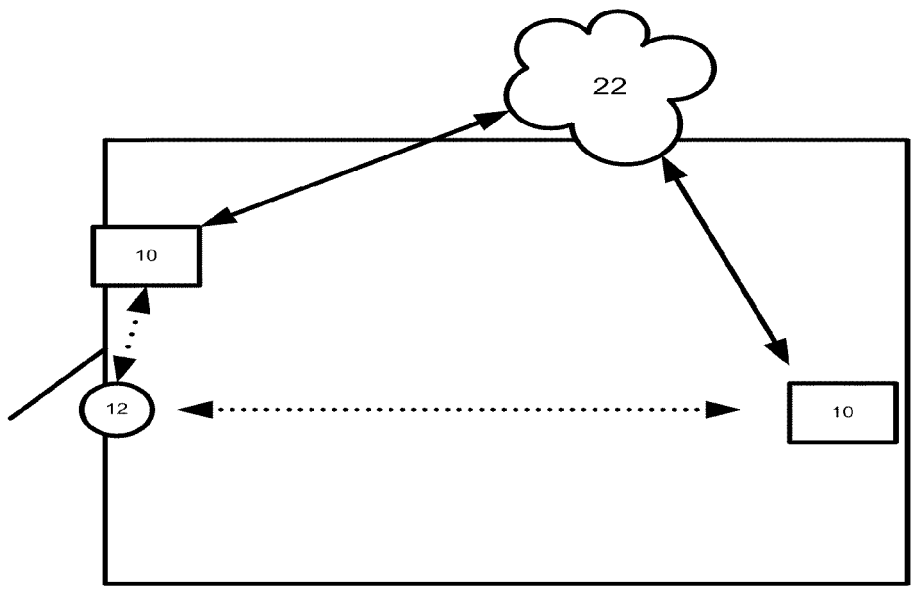
FIG. 1 shows a wireless area network (WAN) that provides occupancy or motion sensing.

FIG. 1 shows a wireless area network that provides motion sensing. A wireless communication transceiver 10 is mounted in a room such as near an entrance. The transceiver 10 includes a sensor to determine whether the room is empty or being used by at least one person 12. The sensor can be implemented in software to provide the motion sensing at a very low cost. A plurality of transceivers 10 form a mesh network 22, which is a communications network having two or more paths to any node. Mesh networking is a way to route data, voice and instructions between nodes. It allows for continuous connections and reconfiguration around blocked paths by "hopping" from node to node until a connection can be established. The transceiver 10 can be an 802.15 (ZigBee) transceiver, but can also be 802.11 (WiFi) transceiver, 802.16 (WiMAX) transceiver, Bluetooth transceiver, cellular transceiver, or cordless telephone transceiver, among others. The transceiver 10 wirelessly communicates with one or more appliances 20 using the mesh network 22. The transceiver 10 controls one or more appliances 20 directly, or alternatively, can send a message to a host device that controls the appliances 20.

In this embodiment, a wireless device such as transceiver 10 transmits a radio frequency (RF) signal and listens for RF signal bouncing back from the walls and other paths. The RF signal is measured as a Received Signal Strength Indicator or Indication (RSSI). The RSSI signal or circuit indicates the strength of the incoming (received) signal in a receiver. RSSI is often done in the IF stage before the IF amplifier. In zero-IF systems, it is done in the baseband signal chain, before the baseband amplifier. RSSI output is often a DC analog level. It can also be sampled by an internal ADC and the resulting codes available directly or via peripheral or internal processor bus.

Signal strength across the RF link varies because of the indoor multi-path environment. A mixture of direct and reflected signal paths results in a time-varying fading characteristic. The RSSI measurements therefore vary in time and follow a statistical model depending on the proportion of direct and indirect rays in the environment. Since up-fades vary less than downfades, a peak-holding algorithm provides a reasonable estimate of average RSSI (FIG. 4) for two static nodes measuring a mobile node crossing at a cell boundary. Due to fading variations there is a 5 dB variability in peak-signal strength, which can be controlled by filtering and hysteresis thresholds.

Based on the RSSI signal, the transceiver detects whether the room is occupied. This is done using only the wireless transceiver circuitry without dedicated sensors such as PIR sensors. The transceiver can then perform time-based control as well as sensor based control. In time-based control, lighting circuits are all routed through a control circuit that switches power on/off based upon preset time schedules or astronomical clocks. In sensor-based control, the control circuit or relays that are integrated into sensors or stand-alone relay (power) packs control the power to individual lights or circuits based upon occupancy and/or daylight.

Figure 2:
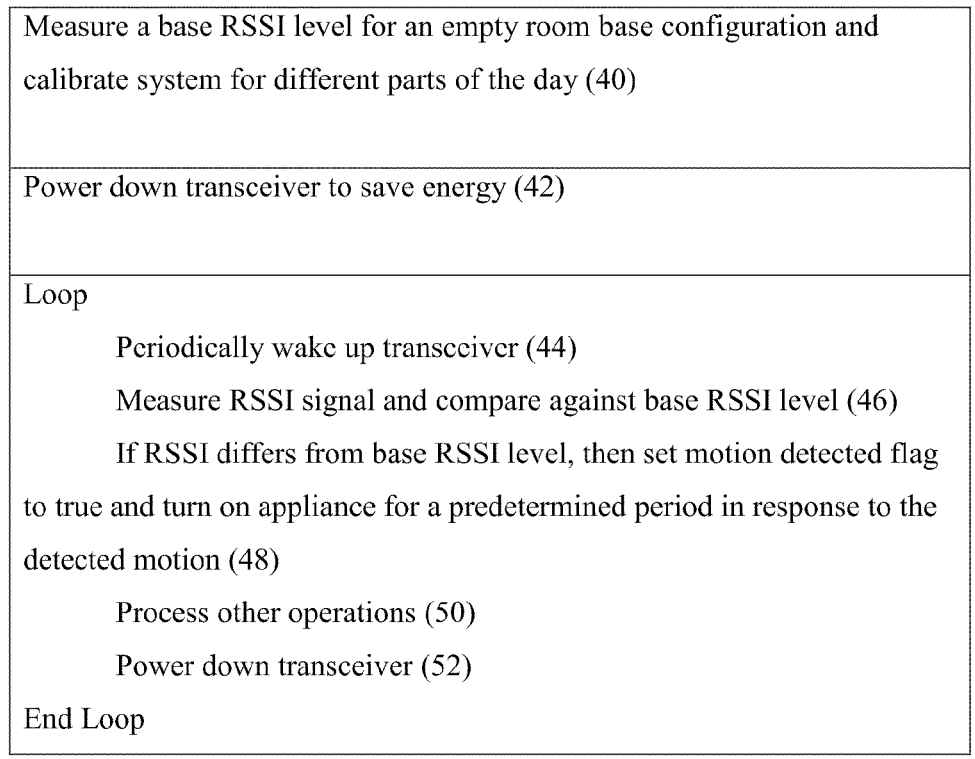
FIG. 2 shows an exemplary process for sensing occupancy or motion using a WAN transceiver.

FIG. 2 shows a process executed by the transceiver 10 to determine motion. In one embodiment, the motion sensing is based on an average Receive Signal Strength Indication (RSSI) signal. In this embodiment, the transceiver 10 is positioned near the entrance and monitors the RSSI signal. When a person is in the room or otherwise is positioned near the antenna of the transceiver 10, the RSSI signal changes in value and the transceiver 10 can detect motion using the RSSI strength as follows:

---

Measure a base RSSI level for an empty room base configuration and calibrate system for different parts of the day (40)
    Optionally power down transceiver to save energy (42)
    Loop
        Periodically wake up transceiver (44)
        Measure RSSI signal and compare against base RSSI level (46)
        If RSSI differs from base RSSI level, then set motion detected flag to true and turn on appliance for a predetermined period in response to the detected motion (48)
        Process other operations (50)
        Optionally power down transceiver (52)
    End Loop

---

The processor for sensing the RSSI can be turned on all the time, or alternatively, can be powered down and periodically be woken up to sense motion. One embodiment measures base RSSI level at different times of the day to improve the accuracy of the motion detection. The RSSI level can change during the day due to periodic fades occurring during hours of the day when the transceivers are affected by solar radiation or other issues. The base RSSI level can be used to handle transmitter variability. Different transmitters behave differently even when they are configured exactly in the same way. When a transmitter is configured to send packets at a power level then the transmitter will send these packets at a power level that is close to that power level but not necessarily equal and this can alter the received signal strength indication and thus it can lead to inaccuracies. The system also accounts for receiver variability: The sensitivity of the receivers across different radio chips is different. In practice, this means that the RSSI value recorded at different receivers can be different even when all the other parameters that affect the received signal strength are kept constant. The base RSSI level takes into consideration the antenna orientation: Each antenna has its own radiation pattern that is not uniform. In practice, this means that the RSSI value recorded at the receiver for a given pair of communicating nodes and for a given distance between them varies as the pair wise antenna orientations of the transmitter and the receiver are changed. Multi-path fading and shadowing in the RF channel are also accounted for. In indoor environments the transmitted signals get reflected after hitting on the walls and/or on other objects in the room such as furniture. Both the original signal and the reflected signal reach the receiver almost at the same time since they both travel at the speed of light. As a result of this, the receiver is not able to distinguish the two signals and it measures the received signal strength for both.

The system can use a plurality of transceivers in a room that coordinates with each other to detect motion more accurately by covering specific areas. For example, as shown in FIG. 1, a transceiver 10 mounted near the room entrance and share information with a transceiver 10 mounted on the opposite side of the room can cooperate to improve the motion sensing process. Since the transceiver 10 performs the motion sensing in software by examining its received signal strength, the motion sensing is implemented at a cost that is nearly zero since only code is loaded into the transceiver 10 in contrast to conventional solutions that require additional costly hardware such as a trip sensor using LED and photosensors or alternatively a Passive Infrared Receivers (PIRs) to detect motion. For the multi-transceiver embodiment, each transceiver 10 can detect motion, and the collective intelligence from all transceivers in the network can be applied to optimize power consumption of the appliances. In the multiple transceiver configuration, each transceiver is already provided in wireless enabled appliance, so the enhanced accuracy of the multi-transceiver embodiment is achieved without additional hardware cost.

For higher accuracy, other schemes can be used such as time-of-flight; angle-of-arrival techniques. The transmitter sends pulses of known duration and intensity. This is accomplished by synchronizing the clocks of the transmitter and receiver. If the transmitter sends data at a known clock cycle, and the receiver gets it at another clock cycle, a distance calculation can be made. The transmitter works continuously at low power, and at 2.4 GHz a 2.5 foot distance resolution can be obtained. To capture the angle of arrival information, the receiver has multiple patch antennas with a plurality of rake fingers which integrate the signal from different sources using a modified CDMA detection process. Prompt, late, early entries received by the rake fingers are correlated to determine arrival angles, not only different multipath conditions. In one embodiment, the system can be set to provide Occupancy Sensor Time Delays, Switch Operation (Manual/Automatic On), Enable/Disable Microphone Occupancy Sensor/Door Sensor/Other Sensor, Custom Device Names, Photocell Setup & Control, 2-Pole Device Settings, Dimming Limits, Remote Firmware Upgrades. The system can also Override Lights ON/OFF, Scheduled ON/OFF, Auto-ON/OFF with Occupancy, Manual ON/OFF via Local Switch, Auto-Dim via LED Sensing, Auto-ON/OFF via LED Sensing, Auto-ON/OFF with Astronomical Clock, Increase Dim Level Decrease Dim Level. The system can also schedule (date/hour/minute) changes to any setting or control mode with convenient recurrence patterns: daily, weekly, weekdays, weekends, etc. Preset and Custom Device Groups selection enable quick programming of zones. The system also provides automatic Daylight Savings Adjustment.

Lobby
   Auto-ON with first occupant
   Permanent ON (no OFFs due to Vacancy) during working hours
   Photocell overrides lights OFF during peak daylight
   Return to occupancy-based control during non-working hours Private Office
   Custom time delays based on occupant requirements
   Lumen maintenance through ceiling dimming photosensor
   User-selected dim levels Open Office
   Requires first morning occupant to initiate Lights ON
   Permanent ON status during working hours
   Standard occupancy control during evening non-working hours
   Short time delays during late night guard walk through Restroom
   2-Pole sensor controls light and fan separately
   Light turns OFF shortly after vacancy; fan runs for extended time
   Varying time delay periods for working vs. non-working hours in order to maintain lamp life while maximizing energy savings Retail Floor
   Occupancy control during early morning stocking hours
   Lights are on Time-of-Day/Day-of-Week schedule during store hours
   Occupancy control during evening cleaning hours
   Occupancy sensors automatically accommodate special late night sales without reprogramming system Classroom
   System accommodates inboard/outboard switching (A/B)
   Stepped dimming or continuous dimming with local set-point control
   Dual Technology (PDT) during class hours, single technology (PIR) and shortened time delays during cleaning periods Parking Garage/Lot
   Astronomical dawn and dusk times available
   Photocell override during daylight hours
   All lights extinguished during times when garage is closed In one embodiment, each person's heartbeat is a virtual fingerprint that can be used to identify one person from another person in the house. As discussed above, suitable statistical recognizers such as Hidden Markov Model (HMM) recognizers, neural network, fuzzy recognizer, dynamic time warp (DTW) recognizer, a Bayesian network, or a Real Analytical Constant Modulus Algorithm (RACMA) recognizer, among others can be used to distinguish one person's heartbeat from another. This technique allows the system to track multiple people in a residence at once. Additionally, three or more transceivers can be positioned in the residence so that their position can be determined through triangulation. The positional data, heart rate, and breathing rate/respiration rate, as well as change delta for each, can be data mined to determine the user's daily activity patterns. A Hidden Markov Model (HMM) recognizer, a dynamic time warp (DTW) recognizer, a neural network, a fuzzy logic engine, or a Bayesian network can be applied to the actual or the difference/change for a particular signal, for example the heart rate or breathing rate, to determine the likelihood of a stroke attack in one embodiment.

Substantially any type of learning system or process may be employed to determine the user's ambulatory and living patterns so that unusual events can be flagged.

In one embodiment, clustering operations are performed to detect patterns in the data. In another embodiment, a neural network is used to recognize each pattern as the neural network is quite robust at recognizing user habits or patterns. Once the treatment features have been characterized, the neural network then compares the input user information with stored templates of treatment vocabulary known by the neural network recognizer, among others. The recognition models can include a Hidden Markov Model (HMM), a dynamic programming model, a neural network, a fuzzy logic, or a template matcher, among others. These models may be used singly or in combination.

Dynamic programming considers all possible points within the permitted domain for each value of i. Because the best path from the current point to the next point is independent of what happens beyond that point. Thus, the total cost of [i(k), j(k)] is the cost of the point itself plus the cost of the minimum path to it. Preferably, the values of the predecessors can be kept in an M×N array, and the accumulated cost kept in a 2×N array to contain the accumulated costs of the immediately preceding column and the current column. However, this method requires significant computing resources. For the recognizer to find the optimal time alignment between a sequence of frames and a sequence of node models, it must compare most frames against a plurality of node models. One method of reducing the amount of computation required for dynamic programming is to use pruning. Pruning terminates the dynamic programming of a given portion of user habit information against a given treatment model if the partial probability score for that comparison drops below a given threshold. This greatly reduces computation.

Considered to be a generalization of dynamic programming, a hidden Markov model is used in the preferred embodiment to evaluate the probability of occurrence of a sequence of observations O(1), O(2), ... O(t), ..., O(T), where each observation O(t) may be either a discrete symbol under the VQ approach or a continuous vector. The sequence of observations may be modeled as a probabilistic function of an underlying Markov chain having state transitions that are not directly observable. In one embodiment, the Markov network is used to model a number of user habits and activities. The transitions between states are represented by a transition matrix A=[a(i,j)]. Each a(i,j) term of the transition matrix is the probability of making a transition to state j given that the model is in state i. The output symbol probability of the model is represented by a set of functions B=[b(j) (O(t)], where the b(j) (O(t) term of the output symbol matrix is the probability of outputting observation O(t), given that the model is in state j. The first state is always constrained to be the initial state for the first time frame of the utterance, as only a prescribed set of left to right state transitions are possible. A predetermined final state is defined from which transitions to other states cannot occur. Transitions are restricted to reentry of a state or entry to one of the next two states. Such transitions are defined in the model as transition probabilities. Although the preferred embodiment restricts the flow graphs to the present state or to the next two states, one skilled in the art can build an HMM model without any transition restrictions, although the sum of all the probabilities of transitioning from any state must still add up to one. In each state of the model, the current feature frame may be identified with one of a set of predefined output symbols or may be labeled probabilistically. In this case, the output symbol probability b(j) O(t) corresponds to the probability assigned by the model that the feature frame symbol is O(t). The model arrangement is a matrix A=[a(i,j)] of transition probabilities and a technique of computing B=b (j) O(t), the feature frame symbol probability in state j. The Markov model is formed for a reference pattern from a plurality of sequences of training patterns and the output symbol probabilities are multivariate Gaussian function probability densities. The patient habit information is processed by a feature extractor. During learning, the resulting feature vector series is processed by a parameter estimator, whose output is provided to the hidden Markov model. The hidden Markov model is used to derive a set of reference pattern templates, each template representative of an identified pattern in a vocabulary set of reference treatment patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator. The HMM template has a number of states, each having a discrete value. However, because treatment pattern features may have a dynamic pattern in contrast to a single value. The addition of a neural network at the front end of the HMM in an embodiment provides the capability of representing states with dynamic values. The input layer of the neural network comprises input neurons. The outputs of the input layer are distributed to all neurons in the middle layer. Similarly, the outputs of the middle layer are distributed to all output states, which normally would be the output layer of the neuron. However, each output has transition probabilities to itself or to the next outputs, thus forming a modified HMM. Each state of the thus formed HMM is capable of responding to a particular dynamic signal, resulting in a more robust HMM. Alternatively, the neural network can be used alone without resorting to the transition probabilities of the HMM architecture.

In one embodiment, the system can operate in a home, a nursing home, or a hospital. In this system, one or more mesh network appliances 8 are provided to enable wireless communication in the home monitoring system. Appliances 8 in the mesh network can include home security monitoring devices, door alarm, window alarm, home temperature control devices, fire alarm devices, among others. Appliances 8 in the mesh network can be one of multiple portable physiological transducer, such as a blood pressure monitor, heart rate monitor, weight scale, thermometer, spirometer, single or multiple lead electrocardiograph (ECG), a pulse oxymeter, a body fat monitor, a cholesterol monitor, a signal from a medicine cabinet, a signal from a drug container, a signal from a commonly used appliance such as a refrigerator/stove/oven/washer, or a signal from an exercise machine, such as a heart rate. For example, within a house, a user may have mesh network appliances that detect window and door contacts, smoke detectors and motion sensors, video cameras, key chain control, temperature monitors, CO and other gas detectors, vibration sensors, and others. A user may have flood sensors and other detectors on a boat. An individual, such as an ill or elderly grandparent, may have access to a panic transmitter or other alarm transmitter. Other sensors and/or detectors may also be included. The user may register these appliances on a central security network by entering the identification code for each registered appliance/device and/or system. The mesh network can be Zigbee network or 802.15 network.

Figure 3:
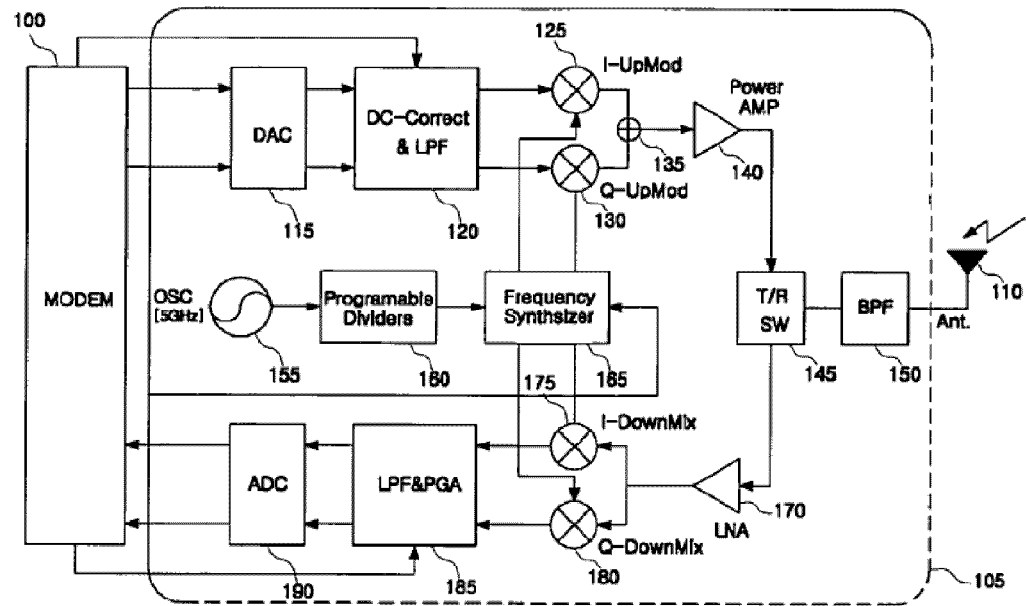
FIG. 3 shows an exemplary transceiver circuit.

FIG. 3 shows an exemplary ZigBee version of the transceiver 10. In the block diagram of a typical ZigBee communication transceiver, a wireless communication transceiver has a BaseBand (BB) modem 100 that performs modulation and demodulation using modulation and demodulation schemes defined by the physical layer specifications of each standard, a Radio Frequency (RF) front-end block (or RF/analog block) 105 that converts a digital modulated signal, output from the modem, into an RF modulated signal and converts an RF modulated signal, received from an antenna 110, into a digital modulated signal, and the antenna 110 that wirelessly transmits and receives the RF modulated signal.

In the transmission operation of the RF front-end block 105, a Digital-Analog Converter (DAC) 115 converts a signal, digitally modulated by the modem 100, into an analog modulated signal according to bit resolution corresponding to a selected standard, and a Direct Current (DC) component correction and Low-Pass Filter (LPF) unit 120 removes a DC offset from the analog modulated signal output from the DAC 115, and low-pass-filters the analog modulated signal to a bandwidth corresponding to a selected transmission standard. Frequency up-converters 125 and 130 up-convert the In-phase (I) component of the BB analog modulated signal, output from the DC component correction and LPF unit 120, and the Quadrature (Q) component thereof into an RF band corresponding to the selected transmission standard, and output I and Q RF modulated signal components, respectively. The I and Q RF modulated signal components are combined together by an adder 135, and the output of the adder 135 is amplified by a power amplifier 140. The RF modulated signal is output to the antenna 110 at transmission periods based on TDD through a transmission/reception switch 145. In this case, the RF modulated signal passes through a Band-Pass Filter (BPF) 150 to allow out-of-band spurious signals to be removed therefrom.

In the reception operation of the RF front-end block 105, the RF modulated signal, input from the antenna 110, is freed from out-of-band spurious signals by the BPF 150, and is input to the transmission/reception switch 145.

The transmission/reception switch 145 outputs the RF modulated signal, output from the power amplifier 140 of a transmission side, toward the antenna 110 through the BPF 150 at the intervals of transmission and reception, or inputs the RF modulated signal, received from the antenna 110 and passed through the BPF 150, to the Low Noise Amplifier 170 of a reception side.

The LNA 170 low-noise-amplifies an analog modulated signal (RF modulated signal) in an RF frequency band. The low-noise-amplified analog modulated signal is down-converted into BB modulated signals by frequency down-conversion mixers 175 and 180 with respect to the I and Q components thereof. A low-pass filter and programmable gain amplifier 185 low-pass-filters the down-converted BB band modulated signal to channel bandwidth corresponding to the transmission standard and performs BB amplification with respect to the I and Q components.

An Analog-Digital Converter (ADC) 190 converts the above-described BB signal into a digital modulated signal according to a bit resolution corresponding to the selected transmission standard, and outputs the digital modulated signal to the BB modem 100.

In regard to the generation of a carrier, a programmable divider 160 diminishes a local oscillation frequency generated by an oscillator 155, and a frequency synthesizer 165 generates a carrier frequency using a frequency output from the programmable divider 160.

Figure 4:
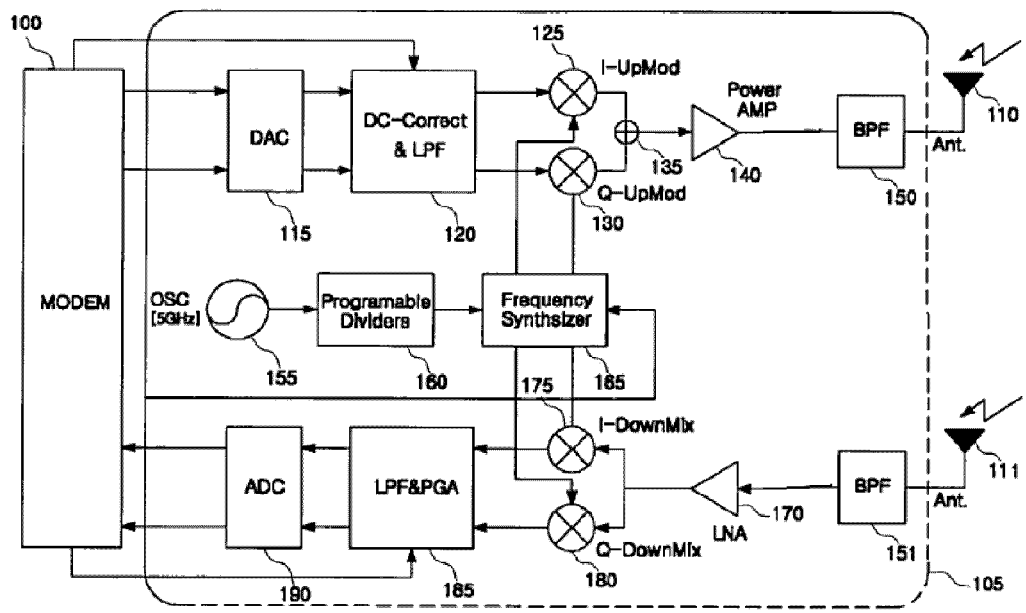
FIG. 4 shows an exemplary transceiver operating as a Doppler radar.

FIG. 4 shows a block diagram of a wireless communication transceiver capable of performing radar sensing of people using Doppler techniques. Although the system is shown for ZigBee transceiver to minimize cost, systems based on WiMAX transceiver or WiFi transceiver can be implemented as well. The embodiment of FIG. 4 is similar to the embodiment of FIG. 1, but with separate transmit antenna 110 and receive antenna 111 and separate bandpass filters 150 and 151, respectively. The separate transmit and receive circuitry allows Doppler detection of the reflected signals. In the Doppler radar phenomenon, the frequency of a radio signal is altered when the signal reflects off of a moving object. In one embodiment, the movement of people is detected. In another embodiment, the periodic movement of the chest and internal organs of the person modulates an incident or transmitted radio signal from one of the wireless transceivers, and the resulting reflection is interpreted to deduce the presence of a person. The reflection can capture fine resolution information about the person who is in range of the transceiver 10. The information can include, for example, heart and breathing activity. Transceivers that operate at high frequencies can be used to provide higher resolution and improved antenna patterns could be used for more detailed observations of arterial motion. The improved arterial motion pattern can be used to distinguish one person from another person using Hidden Markov Model recognizers in one embodiment.

In another embodiment, two separate wireless conventional ZigBee devices are used: one as a transmitter and the other one as a receiver. Separate transmit and receive antennas perform transmission and reception simultaneously. Each wireless adapter can be an 802.15 (ZigBee) adapter that can be wall mounted or placed on suitable furniture. The local oscillators of the adapters are synchronized by providing a common crystal reference to the LO synthesizers in both chip sets. The baseband output of the receiver adapter is prefiltered with a low-pass RC filter with a cut-off frequency of about 100 Hz in one embodiment to remove out of band noise and avoid aliasing error. The pre-filtered signal is digitized and used to calculate heart rate. The digitized signal is the additionally filtered in the digital domain to separate the heart and breathing signals. To determine heart rate, an autocorrelation function was calculated for the heart signal. The periodicity of the autocorrelation function is used to determine the heart rate. A filter can also be applied to extract breathing rate from the digitized signal.

Figure 5:
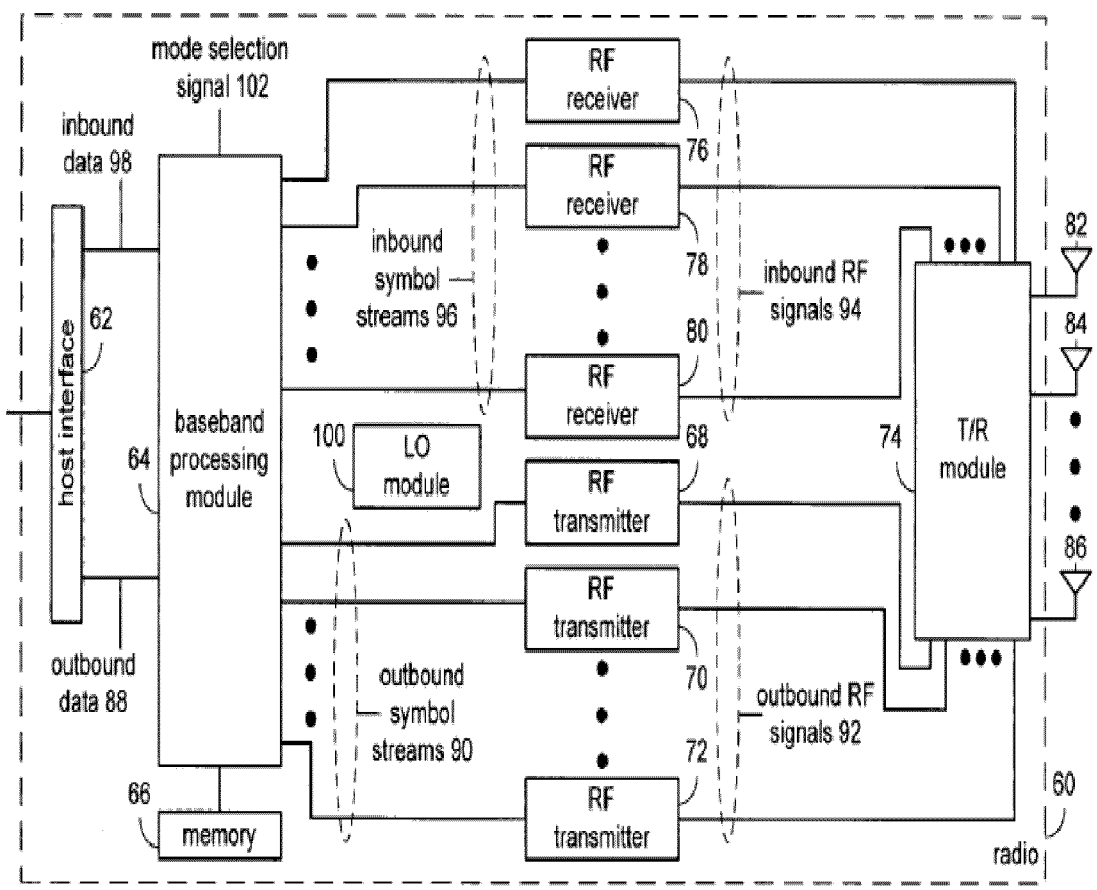
FIG. 5 shows a MIMO transceiver operating as a Doppler radar.

Another embodiment shown in FIG. 5 uses a multiple input, multiple output (MIMO) wireless adapter chip set. The inventor contemplates that the adapter can be ZigBee adapter, but also be 802.11 (WiFi), 802.16 (WiMAX), Bluetooth adapters, cell phones, or cordless telephones.

FIG. 5 is a schematic block diagram illustrating a wireless communication device that uses a MIMO radio 60 as a Doppler radar to detect people and/or organ movement such as heart beat detection. Radio 60 includes a host interface 62, a baseband processing module 64, memory 66, a plurality of radio frequency (RF) transmitters 68-72, a transmit/receive (T/R) module 74, a plurality of antennas 82-86, a plurality of RF receivers 76-80, and a local oscillation module 100. The baseband processing module 64, in combination with operational instructions stored in memory 66, execute digital receiver functions and digital transmitter functions, respectively. The digital receiver functions include, but are not limited to, digital intermediate frequency to baseband conversion, demodulation, constellation demapping, decoding, de-interleaving, fast Fourier transform, cyclic prefix removal, space and time decoding, and/or descrambling. The digital transmitter functions include, but are not limited to, scrambling, encoding, interleaving, constellation mapping, modulation, inverse fast Fourier transform, cyclic prefix addition, space and time encoding, and/or digital baseband to IF conversion. The baseband processing modules 64 may be implemented using one or more processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The memory 66 may be a single memory device or a plurality of memory devices. Such a memory device may be a read-only memory, random access memory, volatile memory, non-volatile memory, static memory, dynamic memory, flash memory, and/or any device that stores digital information. Note that when the processing module 64 implements one or more of its functions via a state machine, analog circuitry, digital circuitry, and/or logic circuitry, the memory storing the corresponding operational instructions is embedded with the circuitry comprising the state machine, analog circuitry, digital circuitry, and/or logic circuitry. A number of the RF transmitters 68-72 will be enabled to convert the outbound symbol streams 90 into outbound RF signals 92. The transmit/receive module 74 receives the outbound RF signals 92 and provides each outbound RF signal to a corresponding antenna 82-86. When the radio 60 is in the receive mode, the transmit/receive module 74 receives one or more inbound RF signals via the antennas 82-86. The T/R module 74 provides the inbound RF signals 94 to one or more RF receivers 76-80. The RF receiver 76-80 converts the inbound RF signals 94 into a corresponding number of inbound symbol streams 96. The baseband processing module 60 receives the inbound symbol streams 90 and converts them into inbound data 98.

In one embodiment, the MIMO transceiver can also be a spread-spectrum microwave motion sensor that can be co-located with other spectrum users without having to set a specific operating frequency.

The non-invasive measuring techniques can be enhanced by the attachment of wireless sensors to critical locations on the body. The body sensor technique allows the return or reflected signal to be more easily isolated from radar clutter effects, and provides a means for sensing additional data not easily derived from a radar signal, such as skin temperature. The body sensors can be as simple as conductive patches that attach to the back of badges and enhance the reflection of the incident radio signal at a particular location. Alternatively, the body sensors are more complex frequency resonant structures, or even oscillating or multiplying semiconductor circuits. Such circuits can alter the reflected radio signal in time and/or frequency, and can impose additional modulated data, which is generated by, for example, skin temperature, bio-electric effects, re-radiated radar effects, and physical acceleration.

A conducting surface will then reflect most of the energy from an incident radio wave. Placing such a surface or patch on a target area of the body, such as the chest or the skin over an artery, will enhance the return of the radar signal from that target area. As one skilled in the art will appreciate, if the physical dimensions of the conducting surface are properly chosen, the path can act as an electrically resonant antenna that provides an enhanced radar return.

In one embodiment, each person's personal information such as hearbeat is a virtual fingerprint that can be used to identify one person from another person in the house. As discussed above, suitable statistical recognizers such as Hidden Markov Model (HMM) recognizers, neural network, fuzzy recognizer, dynamic time warp (DTW) recognizer, a Bayesian network, or a Real Analytical Constant Modulus Algorithm (RACMA) recognizer, among others can be used to distinguish one person's heartbeat from another. This technique allows the system to track multiple people in a residence at once. Additionally, three or more transceivers can be positioned in the residence so that their position can be determined through triangulation.

In one embodiment, a differential pulse Doppler motion sensor provides a range-invariant Doppler response within a range limited region, and no response outside the region. The transmitter transmits a sequence of transmitted bursts of electromagnetic energy to produce a sensor field, the transmitted bursts having burst widths which vary according to a pattern which cause responses to disturbance in the sensor field which also vary according to the pattern. For one example pattern, the transmitted bursts are switched between a first burst width and a second burst width at a pattern frequency. The receiver receives a combination of the transmitted bursts and reflections of the transmitted bursts and produces a combined output. Thus, the combined output indicates a mixing of the transmitted burst with its own reflection. The width of the burst defines the range limit because any reflection which returns after the burst has ended, results in zero mixing.

In another implementation, the transmitter transmits the sequence of transmitted bursts at a transmitter frequency with a burst repetition rate. The transmitter frequency is on the order of gigaHertz, such as between 900 megaHertz and 24 gigaHertz, or for example between about 5 and 6 gigaHertz. The burst repetition rate is on the order of megaHertz, such as for example 1-5 megaHertz, and more preferably 1-3 megaHertz. A burst width control circuit controls the pattern of varying burst widths by switching a burst widths of the transmitted bursts in the sequence between or among a plurality of burst widths according to a pattern. The pattern has for example a characteristic pattern frequency on the order of 10 kiloHertz to 100 kiloHertz. The pattern at which the burst widths are varied can take on a variety of characteristics. In one system, the burst widths are switched between two different burst widths. In other embodiments, the pattern may vary according to a sine wave, a triangle wave, a ramp signal, or a noise modulated signal for example.

Another embodiment is based upon the reflection of sound waves. Sound waves are defined as longitudinal pressure waves in the medium in which they are travelling. Subjects whose dimensions are larger than the wavelength of the impinging sound waves reflect them; the reflected waves are called the echo. If the speed of sound in the medium is known and the time taken for the sound waves to travel the distance from the source to the subject and back to the source is measured, the distance from the source to the subject can be computed accurately. This is the measurement principle of this embodiment. Here the medium for the sound waves is air, and the sound waves used are ultrasonic, since it is inaudible to humans. Assuming that the speed of sound in air is 1100 feet/second at room temperature and that the measured time taken for the sound waves to travel the distance from the source to the subject and back to the source is t seconds, the distance d is computed by the formula $d=1100 \times 12 \times t$ inches. Since the sound waves travel twice the distance between the source and the subject, the actual distance between the source and the subject will be d/2. The devices used to transmit and receive the ultrasonic sound waves in this application are 40-kHz ceramic ultrasonic transducers. The processor drives the transmitter transducer with a 12-cycle burst of 40-kHz square-wave signal derived from the crystal oscillator, and the receiver transducer receives the echo. A timer is configured to count the 40-kHz crystal frequency such that the time measurement resolution is 25 μs. The echo received by the receiver transducer is amplified by an operational amplifier and the amplified output is fed to a comparator input. The comparator senses the presence of the echo signal at its input and triggers a capture of the timer count value to capture a compare register. The capture is done exactly at the instant the echo arrives at the system. The captured count is the measure of the time taken for the ultrasonic burst to travel the distance from the system to the subject and back to the system. The distance in inches from the system to the subject is computed using this measured time and displayed on a two-digit static LCD. Immediately after updating the display, the processor goes to sleep mode to save power and is periodically woken by another time every 205 milliseconds to repeat the measurement cycle and update the display.

Figure 6:
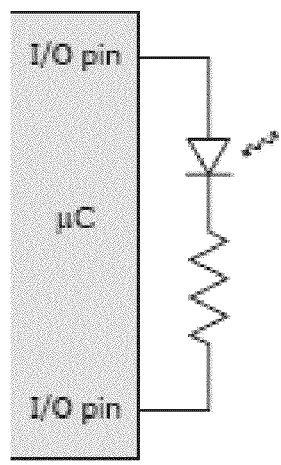
FIG. 6 shows an exemplary LED ambient light sensor.
Figure 6:
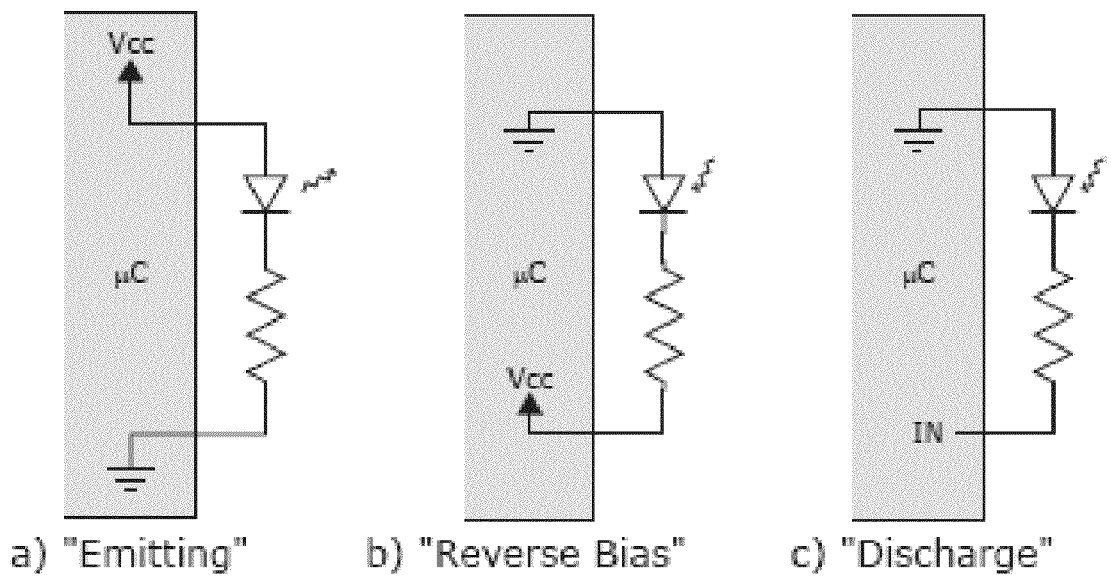

FIG. 6 shows an exemplary LED ambient light sensor. The LED is a photodiode that is sensitive to light at and above the wavelength that which it emits (barring any filtering effects of a colored plastic package). Under reverse bias conditions, a simple model for the LED is a capacitor in parallel with a current source which models the optically induced photocurrent. The system measures the photocurrent. One way to make a photodetector out of an LED is to tie the anode to ground and connect the cathode to a CMOS I/O pin driven high. This reverse biases the diode, and charges the capacitance. Next switch the I/O pin to input mode, which allows the photocurrent to discharge the capacitance down to the digital input threshold. By timing how long this takes, the photocurrent can be measure to determine the amount of incident light. The microprocessor interface technique uses one additional digital I/O pin, but no other additional components compared to those need to simply light the LED. Since the circuit draws only microwatts of power, it has a minimal impact on battery life.

In one embodiment, the LED blinks very fast, and then ambient light is detected when the LED is off. The LED is connected to general IO port GP0 with a resistor between the LED and GP1. When GP0 is high, and GP1 is low, will it conduct, and emit light. When the GP0 is low, and GP1 is high, then the LED is off. The LED is charged to −5V across it, and when the GP1 turns into tri-state and goes low, and the time depends on capacity and on current in LED. A 16-bit Sigma Delta ADC is used to detect the voltage output of the LED when it is off. The voltage output is proportional to the amount of light in the room and can be used to turn on/off room lighting or other peripherals.

FIG. 6A shows the "Emitting" mode where current is driven in the forward direction, lighting the LED. FIG. 6B shows "Reverse Bias" mode, which charges the capacitance and prepares the system for measurement. The actual measurement is made in "Discharge" mode shown in FIG. 6c. Since the current flowing into a CMOS input is extremely small, the low value current limiting resistor has little impact on the voltage seen at the input pin. The system times how long it takes for the photocurrent to discharge the capacitance to the pin's digital input threshold. The result is a simple circuit that can switch between emitting and receiving light. Because the circuit changes required to provide this bidirectional communication feature consist of only one additional I/O pin, adding the light sensor is essentially free.

In one embodiment, a TI MSP430F20x3 microcontroller is used to drive an LED. The LED is used both as an indicator or night light and an ambient room light sensor. The voltage generated by the LED is measured using a built-in 16 bit sigma delta converter. A LED voltage reading is obtained every 200 ms. Based on predefined "Min" and "Max" reference values, the active duty cycle for lighting ballasts is adjusted according to the current light conditions. The darker the ambient light is, the more the ballasts will be set so that room will be illuminated. The microcontroller/LED is exposed to darkness for a short moment in order to calibrate the LED's offset voltage. A very low frequency oscillator (VLO) is used to clock a timer which is used for both PWM generation to adjust LED brightness but also to derive the timings. A calibration process can be implemented to accommodate for variations in VLO frequency.

Figure 7:
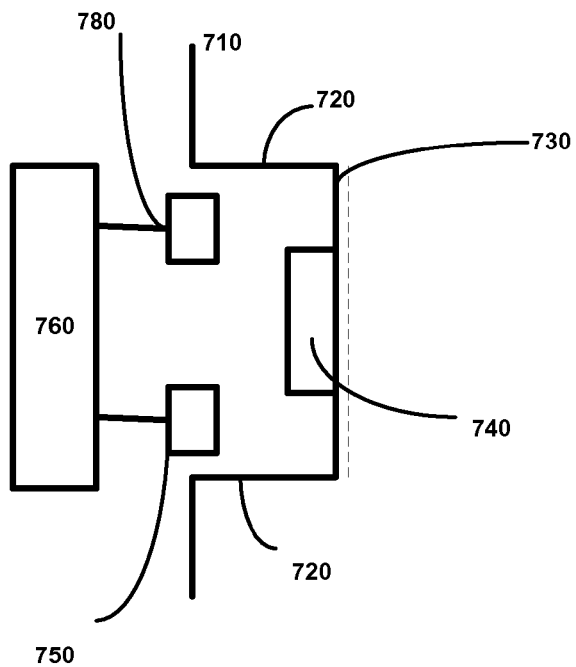
FIG. 7 shows an exemplary LED based microphone to detect sound in the room.

FIG. 7 shows an exemplary LED based microphone to detect sound or noise in the room. In this embodiment, a base surface 710 supports a cylinder that protrudes from the base surface using legs or posts 720. At one end, a flexible membrane 730 is positioned to pick up sound and to vibrate according to noise or sound in the room. A piece of light-reflecting metal foil 740 is positioned on one end. Speech or sound vibrates the foil 740. An LED 750 is directed at the foil 740 and the vibration is reflected off the foil on to the same LED 750 acting as a photocell. Sound is thus captured by the LED 750 and processed by low power a microcontroller 760. The microcontroller 760 is Zigbee transceiver connected to an antenna 780. Radio reflections from occupants in the room cause changes in the RSSI signal which is captured and processed by the controller 780 for occupancy sensing. To aid the LED receiver in detecting the signal, the light source should be pulsed at the highest possible power level. To produce the highest possible light pulse intensity without burning up the LED, a low duty cycle drive must be employed. This can be accomplished by driving the LED with high peak currents with the shortest possible pulse widths and with the lowest practical pulse repetition rate. For standard voice systems, the transmitter circuit can be pulsed at the rate of about 10,000 pulses per second as long as the LED pulse width is less than about 1 microsecond. Such a driving scheme yields a duty cycle (pulse width vs. time between pulses) of less than 1%. However, if the optical transmitter is to be used to deliver only an on/off control signal, then a much lower pulse rate frequency can be used. If a pulse repetition rate of only 50 pps were used, it would be possible to transmit the control message with duty cycle of only 0.005%. Thus, with a 0.005% duty cycle, even if the LED is pulsed to 7 amps the average current would only be about 300 ua. Even lower average current levels are possible with simple on/off control transmitters, if short multi-pulse bursts are used. To obtain the maximum efficiency, the LED should be driven with low loss transistors. Power field effect transistors (FET) can be used to efficiently switch the required high current pulses.

In one embodiment, the LED microphone can be used with the occupancy sensor or detector, providing an ideal solution for areas with obstructions like bathrooms with stalls or open office cubicle areas. This embodiment first detects motion using the wireless radar system and then engages the LED microphone to listen for continued occupancy. The system can tune the sound detection to sudden noise changes only and filters out the background "white" noise.

In another embodiment, the LED microphone can be used with the LED ambient light detector or sunlight sensor/detector. This embodiment first detects ambient room light condition using the LED light sensor and then engages the LED microphone to listen for continued occupancy. The system can tune the sound detection to sudden noise changes only and filters out the background "white" noise.

In another embodiment, the LED microphone can be used with the LED light detector and the LED occupancy sensor or detector. This embodiment first detects if sufficient light exists, then detects people's motion using the wireless radar system and then engages the LED microphone to listen for continued occupancy. The system can tune the sound detection to sudden noise changes only and filters out the background "white" noise.

In yet other embodiments, the clock kept by the microcontroller can be used to supplement the turn on or off of lighting or power other devices in the room. The microcontroller can communicate with a ballast. The ballast is the unit in a fluorescent lighting system that provides power to the fluorescent tube at the proper frequency. Located in the lamp's housing, it is a featureless metal box containing electronic circuitry. Dimmable ballasts are an advanced design that allow lights to be tuned continuously from full brightness to a very low level (usually about five percent of total brightness), to save electricity when less light is needed or to reduce lighting glare.

The system can detect light, sound and people present to provide an accurate determination of occupancy and such determination can be used to effectively provide environmental comforts for the occupants. One exemplary process for room environmental control is as follows:

---

Check clock to see user specified appliance on-off period is met and if so, turn appliance on or off
    Check room light to see if room light is below threshold and if so
        Check room microphone to see if people are present and if so
            Check occupancy sensing radar to sense motion in the room, and if so, turn on one or more appliances such as lighting and display terminals in the room.
    Check room temperature and turn on AC if needed.

A user override button is provided so that the user can manually force the room to turn on appliances as desired.

Figure 8:
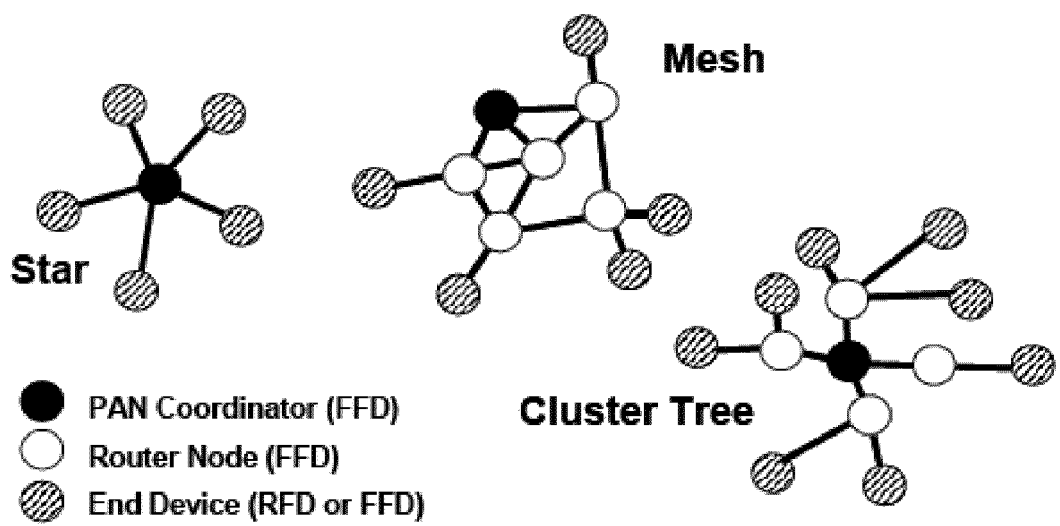
FIG. 8 shows an exemplary mesh network in communication with the occupancy sensing system.
Figure 9:
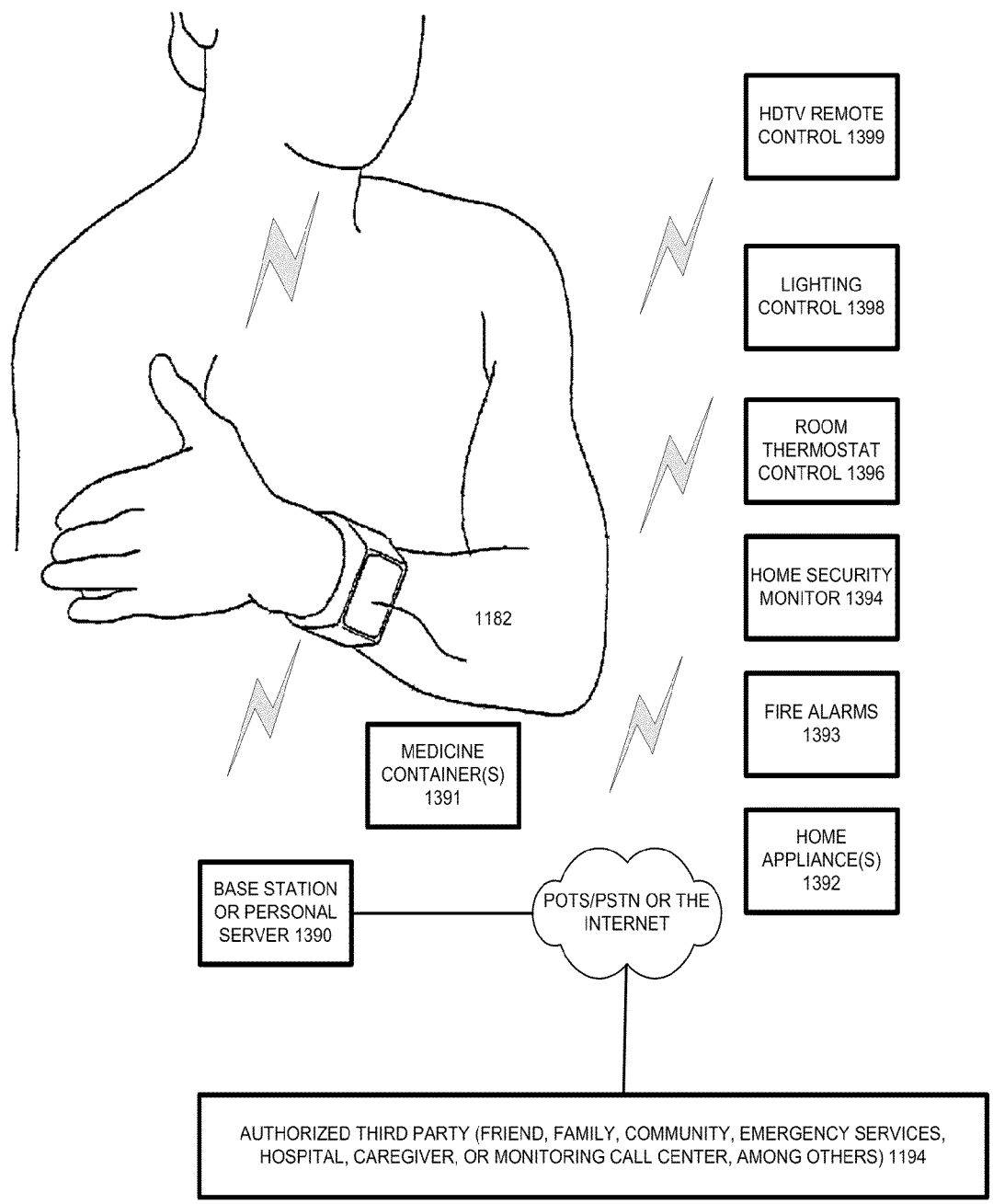
FIG. 9 shows an exemplary mesh network.

FIGS. 8-9 show exemplary mesh networks. Data collected and communicated on the display 1382 of the watch as well as voice is transmitted to a base station 1390 for communicating over a network to an authorized party 1394. The watch and the base station is part of a mesh network that may communicate with a medicine cabinet to detect opening or to each medicine container 1391 to detect medication compliance. Other devices include mesh network thermometers, scales, or exercise devices. The mesh network also includes a plurality of home/room appliances 1392-1399. The ability to transmit voice is useful in the case the patient has fallen down and cannot walk to the base station 1390 to request help. Hence, in one embodiment, the watch captures voice from the user and transmits the voice over the Zigbee mesh network to the base station 1390. The base station 1390 in turn dials out to an authorized third party to allow voice communication and at the same time transmits the collected patient vital parameter data and identifying information so that help can be dispatched quickly, efficiently and error-free. In one embodiment, the base station 1390 is a POTS telephone base station connected to the wired phone network. In a second embodiment, the base station 1390 can be a cellular telephone connected to a cellular network for voice and data transmission. In a third embodiment, the base station 1390 can be a ZigBee, WiMAX or 802.16 standard base station that can communicate VoIP and data over a wide area network. In one implementation, Zigbee or 802.15 appliances communicate locally and then transmits to the wide area network (WAN) such as the Internet over WiFi or WiMAX. Alternatively, the base station can communicate with the WAN over POTS and a wireless network such as cellular or WiMAX or both.

The above described systems can be used to energy efficient control of appliances such as lighting or cooling/heating devices that use energy consumption in a room. The wireless mesh network 22 allows for continuous connections and reconfiguration around blocked paths by hopping from node to node until a connection can be established, the mesh network 22 including one or more wireless area network transceivers 10 adapted to communicate data with the wireless mesh network, the transceiver detecting motion by analyzing reflected wireless signal strength. The appliance 20 is coupled to the transceiver 10 and the appliance is activated or deactivated in response to sensed motion in the room based on the reflected wireless signal strength. For example, if the sensor 12 senses no motion over a period of time, the system turns off non-essential appliances such as the lights and the fan in the room and changes the temperate setting to the lowest cost configuration.

Because each individual emits patterns that are unique to the user, the system can automatically recognize the individuals based on his or her emitted pattern. A recognizer can receive user identifiable characteristics from the transceiver. The recognizer can be a Hidden Markov Model (HMM) recognizer, a dynamic time warp (DTW) recognizer, a neural network, a fuzzy logic engine, or a Bayesian network recognizer, among others.

The recognizer can monitor one or more personally identifiable signatures. For example, the transceiver identifies one person from another based on a heart rate signature as measured by a Doppler radar. A sound transducer such as a microphone and/or a speaker can be connected to the wireless transceiver to communicate audio over a telephone network through the mesh network. A call center or a remote receptionist can be linked to the transceiver to provide a human response. An in-door positioning using triangulation or RSSI-based pattern matching can communicate with one or more mesh network appliances to provide location information. A web server can communicate over the mesh network and to a telephone network to provide information to an authorized remote user. A wireless router can be coupled to the mesh network and wherein the wireless router comprises one of: 802.11 router, 802.16 router, WiFi router, WiMAX router, Bluetooth router, X10 router.

A mesh network appliance can be connected to a power line to communicate data to and from the mesh network. A smart meter can relay data to a utility over the power line and the mesh network to the appliance. The smart meter includes bi-directional communication, power measurement and management capability, software-controllable disconnect switch, and communication over low voltage power line. A remote processor that can remotely turn power on or off to a customer, read usage information from a meter, detect a service outage, detect the unauthorized use of electricity, change the maximum amount of electricity that a customer can demand at any time; and remotely change the meters billing plan from credit to prepay as well as from flat-rate to multi-tariff. The appliance minimizes operating cost by shifting energy use to an off-peak period in response to utility pricing that varies energy cost by time of day. A rechargeable energy reservoir such as a fuel cell or a battery can supply energy to the appliance, and the reservoir is charged during a utility off-peak period and used during a utility peak pricing period. Solar panels, wind mill, or other sources of renewable energy can be provided outside the premises to generate local energy that recharges the reservoir or store energy in the utility grid.

The appliance's operation is customized to each individual's preference since the system can identify each individual through his or her heart rate signature, among others. Each user can set his or her preferences and the system can detect the user's entry into a room and automatically customizes the room to the user. For example, upon entry into a room, the network can stream the user's preferred music into a music player in the room or alternatively can stream his or her favorite TV shows and display on a screen for the user. Also, lighting level and temperature can be customized to the user's preferences. The bed setting can be customized to reflect the user's preference for a soft or hard mattress setting. The chair height, tilt/reclination and firmness can be adjusted to the user's preference. The window transparency or tint can be automatically set to the user's preferred room brightness. Phone calls can automatically be routed to the user's current position. If there are many people in the room, the appliance's operation is customized to a plurality of individuals in a room by clusterizing all preferences and determining a best fit preference from all preferences.

Since the system can track user position quite accurately, the system can store and analyze personal information including medicine taking habits, eating and drinking habits, sleeping habits, or excise habits. The information can be used to track the user's general health.

For users that are at risk of stroke, the positional data, heart rate, and breathing rate/respiration rate, as well as change delta for each, can be data mined to determine the user's daily activity patterns. A Hidden Markov Model (HMM) recognizer, a dynamic time warp (DTW) recognizer, a neural network, a fuzzy logic engine, or a Bayesian network can be applied to the actual or the difference/change for a particular signal, for example the heart rate or breathing rate, to determine the likelihood of a stroke attack in one embodiment.

In another embodiment, a Doppler radar positioned near the heart can pick up the heart beat corresponding to as the S1-S4 heart sounds and determine the likelihood of a stroke from the heart movements that generate the sound patterns for S1-S4. The progression of heart failure (HF) is typically accompanied by changes in heart sounds over time. First, an S4 heart sound may develop while the heart is still relatively healthy. Second, the S4 heart sound becomes more pronounced. Third, as deterioration of the left ventricle continues, S3 heart sounds become more pronounced. Sometimes, this is accompanied by a decrease in S1 heart sounds due to a decrease in the heart's ability to contract. Thus, ongoing or continuous monitoring of heart sounds would greatly assist caregivers in monitoring heart disease. However, individual patients may exhibit unique heart sounds that complicate a generalized approach to heart sound monitoring. For example, the mere presence of an S4 heart sound is not necessarily indicative of heart disease because normal patients may have an S4 heart sound. Another complication develops if a patient experiences atrial fibrillation when an ischemia occurs. In this case a strong atrial contraction, and the associated S4 heart sound, is likely to be absent due to the atrial fibrillation. This results in an increase in the S3 heart sound without an associated S4 heart sound or without an increase in an S4 heart sound. Therefore, the progression of heart disease, such as HF and an ischemic event, is typically better monitored by establishing a patient-specific control baseline heart sound measurement and then monitoring for changes from that baseline. The baseline could be established in one or several different criteria, such as at particular physiologic or pathophysiologic state, at a specific posture, at a particular time of day, etc.

The mesh network comprises code to store and analyze personal information including heart rate, respiration rate, medicine taking habits, eating and drinking habits, sleeping habits, or excise habits, among others.

In one embodiment for home monitoring, the user's habits and movements can be determined by the system for fall or stroke detection. This is done by tracking location, ambulatory travel vectors and time in a database. If the user typically sleeps between 10 pm to 6 am, the location would reflect that the user's location maps to the bedroom between 10 pm and 6 am. In one exemplary system, the system builds a schedule of the user's activity as follows:

| Location | Time Start | Time End | Heart Rate |
| --- | --- | --- | --- |
| Bed room | 10 pm | 6 am | 60-80 |
| Gym room | 6 am | 7 am | 90-120 |
| Bath room | 7 am | 7:30 am | 85-120 |
| Dining room | 7:30 am | 8:45 am | 80-90 |
| Home Office | 8:45 am | 11:30 am | 85-100 |
| ... | | | |
| ... | | | |

The habit tracking is adaptive in that it gradually adjusts to the user's new habits. If there are sudden changes, the system flags these sudden changes for follow up. For instance, if the user spends three hours in the bathroom, the system prompts the third party (such as a call center) to follow up with the patient to make sure he or she does not need help.

In one embodiment, data driven analyzers may be used to track the patient's habits. These data driven analyzers may incorporate a number of models such as parametric statistical models, non-parametric statistical models, clustering models, nearest neighbor models, regression methods, and engineered (artificial) neural networks. Prior to operation, data driven analyzers or models of the patient's habits or ambulation patterns are built using one or more training sessions. The data used to build the analyzer or model in these sessions are typically referred to as training data. As data driven analyzers are developed by examining only training examples, the selection of the training data can significantly affect the accuracy and the learning speed of the data driven analyzer. One approach used heretofore generates a separate data set referred to as a test set for training purposes. The test set is used to avoid overfitting the model or analyzer to the training data. Overfitting refers to the situation where the analyzer has memorized the training data so well that it fails to fit or categorize unseen data. Typically, during the construction of the analyzer or model, the analyzer's performance is tested against the test set. The selection of the analyzer or model parameters is performed iteratively until the performance of the analyzer in classifying the test set reaches an optimal point. At this point, the training process is completed. An alternative to using an independent training and test set is to use a methodology called cross-validation. Cross-validation can be used to determine parameter values for a parametric analyzer or model for a non-parametric analyzer. In cross-validation, a single training data set is selected. Next, a number of different analyzers or models are built by presenting different parts of the training data as test sets to the analyzers in an iterative process. The parameter or model structure is then determined on the basis of the combined performance of all models or analyzers. Under the cross-validation approach, the analyzer or model is typically retrained with data using the determined optimal model structure.

In general, multiple dimensions of a user's daily activities such as start and stop times of interactions of different interactions are encoded as distinct dimensions in a database. A predictive model, including time series models such as those employing autoregression analysis and other standard time series methods, dynamic Bayesian networks and Continuous Time Bayesian Networks, or temporal Bayesian-network representation and reasoning methodology, is built, and then the model, in conjunction with a specific query makes target inferences.

Bayesian networks provide not only a graphical, easily interpretable alternative language for expressing background knowledge, but they also provide an inference mechanism; that is, the probability of arbitrary events can be calculated from the model. Intuitively, given a Bayesian network, the task of mining interesting unexpected patterns can be rephrased as discovering item sets in the data which are much more—or much less—frequent than the background knowledge suggests. These cases are provided to a learning and inference subsystem, which constructs a Bayesian network that is tailored for a target prediction. The Bayesian network is used to build a cumulative distribution over events of interest.

In another embodiment, a genetic algorithm (GA) search technique can be used to find approximate solutions to identifying the user's habits. Genetic algorithms are a particular class of evolutionary algorithms that use techniques inspired by evolutionary biology such as inheritance, mutation, natural selection, and recombination (or crossover). Genetic algorithms are typically implemented as a computer simulation in which a population of abstract representations (called chromosomes) of candidate solutions (called individuals) to an optimization problem evolves toward better solutions. Traditionally, solutions are represented in binary as strings of 0s and 1s, but different encodings are also possible. The evolution starts from a population of completely random individuals and happens in generations. In each generation, the fitness of the whole population is evaluated, multiple individuals are stochastically selected from the current population (based on their fitness), modified (mutated or recombined) to form a new population, which becomes current in the next iteration of the algorithm.

The system allows patients to conduct a low-cost, comprehensive, real-time monitoring of their parameters such as ambulation and falls. Information can be viewed using an Internet-based website, a personal computer, or simply by viewing a display on the monitor. Data measured several times each day provide a relatively comprehensive data set compared to that measured during medical appointments separated by several weeks or even months. This allows both the patient and medical professional to observe trends in the data, such as a gradual increase or decrease in blood pressure, which may indicate a medical condition. The invention also minimizes effects of white coat syndrome since the monitor automatically makes measurements with basically no discomfort; measurements are made at the patient's home or work, rather than in a medical office. The user may give permission to others as needed to read or edit their personal data or receive alerts. The user or clinician could have a list of people that they want to monitor and have it show on their "My Account" page, which serves as a local central monitoring station in one embodiment. Each person may be assigned different access rights which may be more or less than the access rights that the patient has. For example, a doctor or clinician could be allowed to edit data for example to annotate it, while the patient would have read-only privileges for certain pages. An authorized person could set the reminders and alerts parameters with limited access to others.

The server may communicate with a business process outsourcing (BPO) company or a call center to provide central monitoring in an environment where a small number of monitoring agents can cost effectively monitor multiple people 24 hours a day. A call center agent, a clinician or a nursing home manager may monitor a group or a number of users via a summary "dashboard" of their readings data, with ability to drill-down into details for the collected data. A clinician administrator may monitor the data for and otherwise administer a number of users of the system. A summary "dashboard" of readings from all Patients assigned to the Administrator is displayed upon log in to the Portal by the Administrator. Readings may be color coded to visually distinguish normal vs. readings that have generated an alert, along with description of the alert generated. The Administrator may drill down into the details for each Patient to further examine the readings data, view charts etc. in a manner similar to the Patient's own use of the system. The Administrator may also view a summary of all the appliances registered to all assigned Patients, including but not limited to all appliance identification information. The Administrator has access only to information about Patients that have been assigned to the Administrator by a Super Administrator. This allows for segmenting the entire population of monitored Patients amongst multiple Administrators. The Super Administrator may assign, remove and/or reassign Patients amongst a number of Administrators.

In one embodiment, the server provides a web services that communicate with third party software through an interface. In one implementation, telephones and switching systems in call centers are integrated with the home mesh network to provide for, among other things, better routing of telephone calls, faster delivery of telephone calls and associated information, and improved service with regard to client satisfaction through computer-telephony integration (CTI). CTI implementations of various design and purpose are implemented both within individual call-centers and, in some cases, at the telephone network level. For example, processors running CTI software applications may be linked to telephone switches, service control points (SCPs), and network entry points within a public or private telephone network. At the call-center level, CTI-enhanced processors, data servers, transaction servers, and the like, are linked to telephone switches and, in some cases, to similar CTI hardware at the network level, often by a dedicated digital link. CTI processors and other hardware within a call-center is commonly referred to as customer premises equipment (CPE). It is the CTI processor and application software is such centers that provides computer enhancement to a call center. In a CTI-enhanced call center, telephones at agent stations are connected to a central telephony switching apparatus, such as an automatic call distributor (ACD) switch or a private branch exchange (PBX). The agent stations may also be equipped with computer terminals such as personal computer/video display unit's (PC/VDU's) so that agents manning such stations may have access to stored data as well as being linked to incoming callers by telephone equipment. Such stations may be interconnected through the PC/VDUs by a local area network (LAN). One or more data or transaction servers may also be connected to the LAN that interconnects agent stations. The LAN is, in turn, typically connected to the CTI processor, which is connected to the call switching apparatus of the call center.

When a call from a patient arrives at a call center, whether or not the call has been pre-processed at an SCP, the telephone number of the calling line and the medical record are made available to the receiving switch at the call center by the network provider. This service is available by most networks as caller-ID information in one of several formats such as Automatic Number Identification (ANI). Typically the number called is also available through a service such as Dialed Number Identification Service (DNIS). If the call center is computer-enhanced (CTI), the phone number of the calling party may be used as a key to access additional medical and/or historical information from a customer information system (CIS) database at a server on the network that connects the agent workstations. In this manner information pertinent to a call may be provided to an agent, often as a screen pop on the agent's PC/VDU.

The call center enables any of a first plurality of physician or health care practitioner terminals to be in audio communication over the network with any of a second plurality of patient wearable appliances. The call center will route the call to a physician or other health care practitioner at a physician or health care practitioner terminal and information related to the patient (such as an electronic medical record) will be received at the physician or health care practitioner terminal via the network. The information may be forwarded via a computer or database in the practicing physician's office or by a computer or database associated with the practicing physician, a health care management system or other health care facility or an insurance provider. The physician or health care practitioner is then permitted to assess the patient, to treat the patient accordingly, and to forward updated information related to the patient (such as examination, treatment and prescription details related to the patient's visit to the patient terminal) to the practicing physician via the network 200.

In one embodiment, the wireless nodes convert freely available energy inherent in most operating environments into conditioned electrical power. Energy harvesting is defined as the conversion of ambient energy into usable electrical energy. When compared with the energy stored in common storage elements, like batteries and the like, the environment represents a relatively inexhaustible source of energy. Energy harvesters can be based on piezoelectric devices, solar cells or electromagnetic devices that convert mechanical vibrations.

Power generation with piezoelectrics can be done with vibrations on the air vent. The vibration energy harvester consists of three main parts. A piezoelectric transducer (PZT) serves as the energy conversion device, a specialized power converter rectifies the resulting voltage, and a capacitor or battery stores the power. The PZT takes the form of an aluminum cantilever with a piezoelectric patch. The vibration-induced strain in the PZT produces an ac voltage. The system repeatedly charges a battery or capacitor, which then operates the motor and/or other sensors at a relatively low duty cycle. The energy is converted and stored in a low-leakage charge circuit until a predetermined threshold voltage is reached. Once the threshold is reached, the regulated power is allowed to flow for a sufficient period to power the wireless node such as the Zigbee CPU/transceiver. The transmission is detected by nearby wireless nodes that are AC-powered and forwarded to the base station for signal processing. Power comes from the vibration of the system being monitored and the unit requires no maintenance, thus reducing life-cycle costs. In one embodiment, the housing of the unit can be PZT composite, thus reducing the weight.

For wireless nodes that require more power, electromagnetics, including coils, magnets, and a resonant beam, and micro-generators can be used to produce electricity from readily available vibratory sources. Typically, a transmitter needs about 30 mW, but the device transmits for only tens of milliseconds, and a capacitor in the circuit can be charged using harvested energy and the capacitor energy drives the wireless transmission, which is the heaviest power requirement. Electromagnetic energy harvesting uses a magnetic field to convert mechanical energy to electrical. A coil attached to the oscillating mass traverses through a magnetic field that is established by a stationary magnet. The coil travels through a varying amount of magnetic flux, inducing a voltage according to Faraday's law. The induced voltage is inherently small and must therefore be increased to viably source energy. Methods to increase the induced voltage include using a transformer, increasing the number of turns of the coil, and/or increasing the permanent magnetic field. Electromagnetic devices use the motion of a magnet relative to a wire coil to generate an electric voltage. A permanent magnet is placed inside a wound coil. As the magnet is moved through the coil it causes a changing magnetic flux. This flux is responsible for generating the voltage which collects on the coil terminals. This voltage can then be supplied to an electrical load. Because an electromagnetic device needs a magnet to be sliding through the coil to produce voltage, energy harvesting through vibrations is an ideal application. In one embodiment, electromagnetic devices are placed inside the heel of a shoe. One implementation uses a sliding magnet-coil design, the other, opposing magnets with one fixed and one free to move inside the coil. If the length of the coil is increased, which increases the turns, the device is able to produce more power.

In an electrostatic (capacitive) embodiment, energy harvesting relies on the changing capacitance of vibration-dependant varactors. A varactor, or variable capacitor, is initially charged and, as its plates separate because of vibrations, mechanical energy is transformed into electrical energy. MEMS variable capacitors are fabricated through silicon micro-machining techniques.

In another embodiment, the wireless node can be powered from thermal and/or kinetic energy. Temperature differentials between opposite segments of a conducting material result in heat flow and consequently charge flow, since mobile, high-energy carriers diffuse from high to low concentration regions. Thermopiles consisting of n- and p-type materials electrically joined at the high-temperature junction are therefore constructed, allowing heat flow to carry the dominant charge carriers of each material to the low temperature end, establishing in the process a voltage difference across the base electrodes. The generated voltage and power is proportional to the temperature differential and the Seebeck coefficient of the thermoelectric materials. Body heat from a user's wrist is captured by a thermoelectric element whose output is boosted and used to charge the a lithium ion rechargeable battery. The unit utilizes the Seeback Effect which describes the voltage created when a temperature difference exists across two different metals. The thermoelectric generator takes body heat and dissipates it to the ambient air, creating electricity in the process.

Another embodiment extracts energy from the surrounding environment using a small rectanna (microwave-power receivers or ultrasound power receivers) placed in patches or membranes on the skin or alternatively injected underneath the skin. The rectanna converts the received emitted power back to usable low frequency/dc power. A basic rectanna consists of an antenna, a low pass filter, an ac/dc converter and a dc bypass filter. The rectanna can capture renewable electromagnetic energy available in the radio frequency (RF) bands such as AM radio, FM radio, TV, very high frequency (VHF), ultra high frequency (UHF), global system for mobile communications (GSM), digital cellular systems (DCS) and especially the personal communication system (PCS) bands, and unlicensed ISM bands such as 2.4 GHz and 5.8 GHz bands, among others. The system captures the ubiquitous electromagnetic energy (ambient RF noise and signals) opportunistically present in the environment and transforming that energy into useful electrical power. The energy-harvesting antenna is preferably designed to be a wideband, omnidirectional antenna or antenna array that has maximum efficiency at selected bands of frequencies containing the highest energy levels. In a system with an array of antennas, each antenna in the array can be designed to have maximum efficiency at the same or different bands of frequency from one another. The collected RF energy is then converted into usable DC power using a diode-type or other suitable rectifier. This power may be used to drive, for example, an amplifier/filter module connected to a second antenna system that is optimized for a particular frequency and application. One antenna system can act as an energy harvester while the other antenna acts as a signal transmitter/receiver. The antenna circuit elements are formed using standard wafer manufacturing techniques. The antenna output is stepped up and rectified before presented to a trickle charger. The charger can recharge a complete battery by providing a larger potential difference between terminals and more power for charging during a period of time. If battery includes individual micro-battery cells, the trickle charger provides smaller amounts of power to each individual battery cell, with the charging proceeding on a cell by cell basis. Charging of the battery cells continues whenever ambient power is available. As the load depletes cells, depleted cells are switched out with charged cells. The rotation of depleted cells and charged cells continues as required. Energy is banked and managed on a microcell basis.

In a solar cell embodiment, photovoltaic cells convert incident light into electrical energy. Each cell consists of a reverse biased pn+ junction, where light interfaces with the heavily doped and narrow n+ region. Photons are absorbed within the depletion region, generating electron-hole pairs. The built-in electric field of the junction immediately separates each pair, accumulating electrons and holes in the n+ and p-regions, respectively, and establishing in the process an open circuit voltage. With a load connected, accumulated electrons travel through the load and recombine with holes at the p-side, generating a photocurrent that is directly proportional to light intensity and independent of cell voltage.

As the energy-harvesting sources supply energy in irregular, random "bursts," an intermittent charger waits until sufficient energy is accumulated in a specially designed transitional storage such as a capacitor before attempting to transfer it to the storage device, lithium-ion battery, in this case. Moreover, the system must partition its functions into time slices (time-division multiplex), ensuring enough energy is harvested and stored in the battery before engaging in power-sensitive tasks. Energy can be stored using a secondary (rechargeable) battery and/or a supercapacitor. The different characteristics of batteries and supercapacitors make them suitable for different functions of energy storage. Supercapacitors provide the most volumetrically efficient approach to meeting high power pulsed loads. If the energy must be stored for a long time, and released slowly, for example as back up, a battery would be the preferred energy storage device. If the energy must be delivered quickly, as in a pulse for RF communications, but long term storage is not critical, a supercapacitor would be sufficient. The system can employ i) a battery (or several batteries), ii) a supercapacitor (or supercapacitors), or iii) a combination of batteries and supercapacitors appropriate for the application of interest. In one embodiment, a microbattery and a microsupercapacitor can be used to store energy. Like batteries, supercapacitors are electrochemical devices; however, rather than generating a voltage from a chemical reaction, supercapacitors store energy by separating charged species in an electrolyte. In one embodiment, a flexible, thin-film, rechargeable battery from Cymbet Corp. of Elk River, Minn. provides 3.6V and can be recharged by a reader. The battery cells can be from 5 to 25 microns thick. The batteries can be recharged with solar energy, or can be recharged by inductive coupling. The tag is put within range of a coil attached to an energy source. The coil "couples" with the antenna on the RFID tag, enabling the tag to draw energy from the magnetic field created by the two coils.

As one of average skill in the art will appreciate, the wireless communication devices described above may be implemented using one or more integrated circuits. For example, a host device may be implemented on one integrated circuit, the baseband processing module may be implemented on a second integrated circuit, and the remaining components of the radio, less the antennas, may be implemented on a third integrated circuit. As an alternate example, the radio may be implemented on a single integrated circuit. As yet another example, the processing module of the host device and the baseband processing module may be a common processing device implemented on a single integrated circuit.

Figure 10:
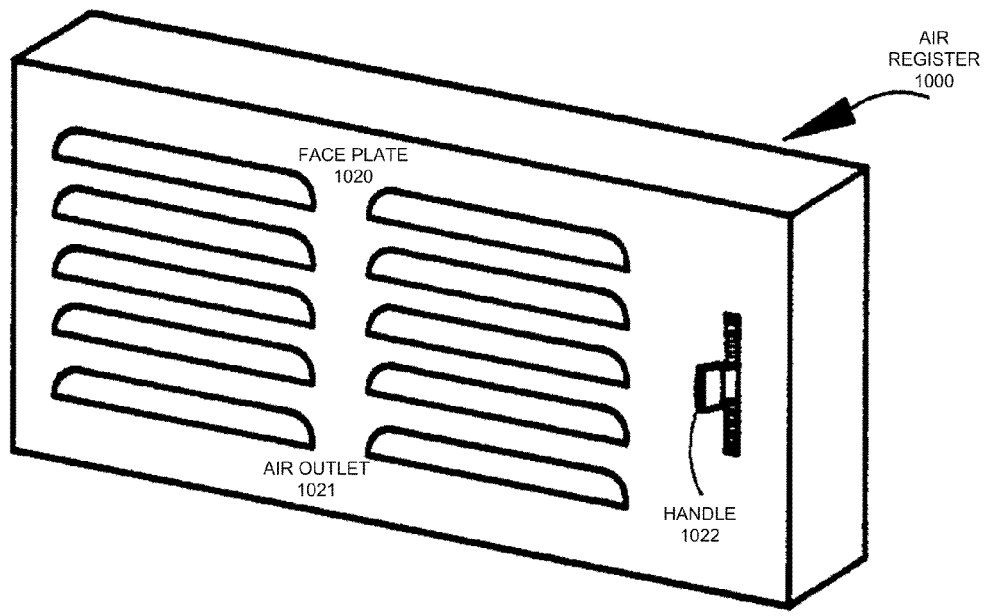
FIG. 10 shows an exemplary smart air vent or air register.

FIG. 10 shows an exemplary air register 1000. The air register 1000 has a face plate 1020 with a plurality of outlets 1021 and a handle 1022 for a user to manually adjust vent openings and adjust air flow as desired. The handle 1022 is supplemented by a wirelessly controlled actuator such as a motor, as described in more details below. The air register 1000 can be made of lightweight plastic, aluminum, or other metal. Screw holes can be placed anywhere along the side margin of the air register 1000 for installation of the device on existing register slots.

Figure 11:
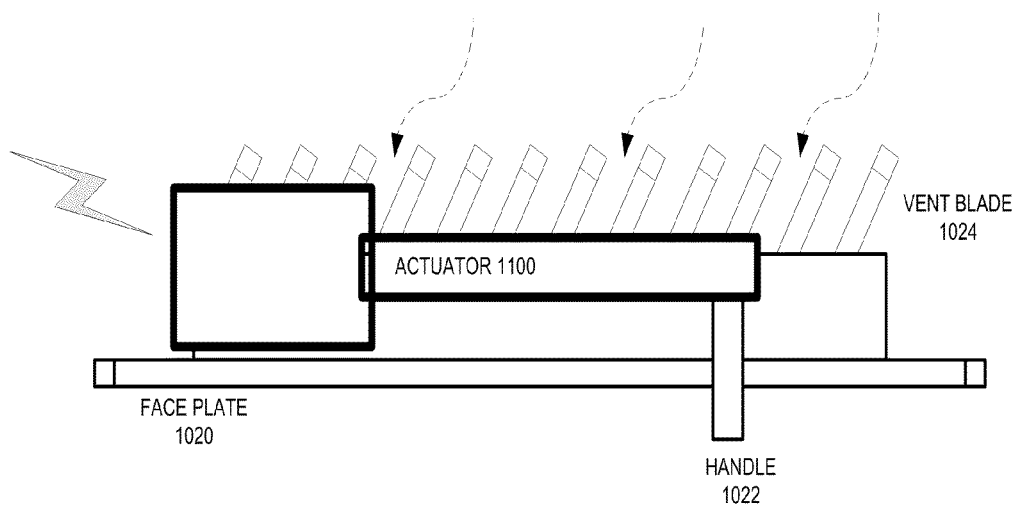
FIG. 11 shows a cross-sectional view of the register of FIG. 10.

FIG. 11 shows a side view of the register of FIG. 10. An actuator 1100 is mounted above the face place 1020 and pivotably connected to the handle 1022. The actuator 1100 can be a motor, solenoid, or an electrical latch, for example. As shown in FIG. 11, a plurality of vent blades 1024 are in the OPEN position to allow air flow to traverse the register 1000. In this manner, either a user or the actuator 1100 can open/close the vent blades 1024. In one embodiment, to provide for attractive styling, the register depth or thickness dimension has been made as shallow as permissible by the size of the actuating lever 1022, yet without having the actuating lever exposed.

To permit the size and shape of air register to be as compact as desired, it is important that the individual components within the actuator 1100 be low profile. In practical reality, this concern is only important in respect to the battery and the motor. The electrical power required to be supplied from the built-in battery must be modest enough to permit this battery to be small enough to reasonably fit within the desired specified dimensions of the controller means. Similarly, the mechanical power required to be supplied by the built-in motor must be modest enough to permit this motor to be small enough to reasonably fit within the specified dimensions.

Since a certain amount of energy is required to effect actuation of the actuation lever, the power required is inversely proportional to the time allowed to effect this actuation. Thus, by way of a speed-reducing gear mechanism, it becomes possible to actuate the actuation lever at an arbitrarily small power level.

By allowing complete OPEN-to-CLOSED and CLOSED-to-OPEN actuation to take place over a period of some ten seconds from start to finish, the motor power output requirement gets to be acceptably modest; and actuation can then readily be accomplished by way of a substantially conventional miniature DC motor.

As another consequence of allowing as long as ten seconds to effect full actuation of the air register, the electrical power required by the motor now becomes adequately modest to permit the use of two AA size batteries. Thus, by trading time for power, the motor and a gear can be made small and require low power to move the vent blades. In another embodiment, a supercapacitor can be used. In another embodiment, solar cells can provide power to actuate the air register.

FIGS. 12A-12D show exemplary control electronics for the air register 1000. Turning now FIG. 12A, a single chip 1100 that contains a processor, ROM/RAM, and a Zigbee transceiver is connected to an antenna 1111. The control chip 1100 is connected to a driver 1112 which is connected to an actuator 1114 such as a motor that actuates movement by the air register 1000. One exemplary single chip device is the Texas Instrument CC2530, which is a true system-on-chip (SoC) solution for IEEE 802.15.4, Zigbee and RF4CE applications. It enables robust network nodes to be built with very low total bill-of-material costs. The CC2530 combines the excellent performance of a leading RF transceiver with an industry-standard enhanced 8051 MCU, in-system programmable flash memory, 8-KB RAM, and many other powerful features. The CC2530 comes in four different flash versions: CC2530F32/64/128/256, with 32/64/128/256 KB of flash memory, respectively. The CC2530 has various operating modes, making it highly suited for systems where ultralow power consumption is required. Short transition times between operating modes further ensure low energy consumption.

Figure 12A:
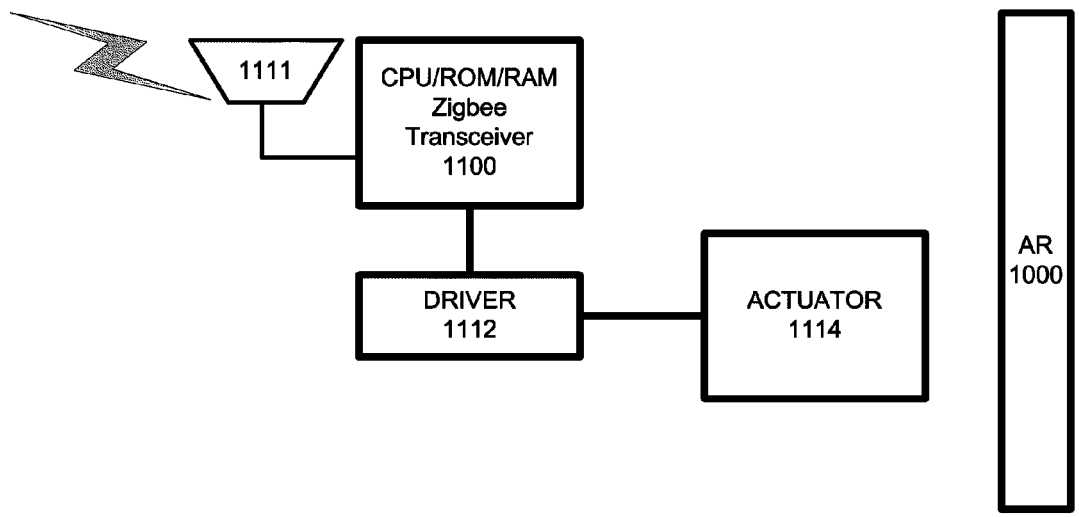
FIG. 12A-D shows exemplary electronics controlling the air register of FIG. 10.
Figure 12B:
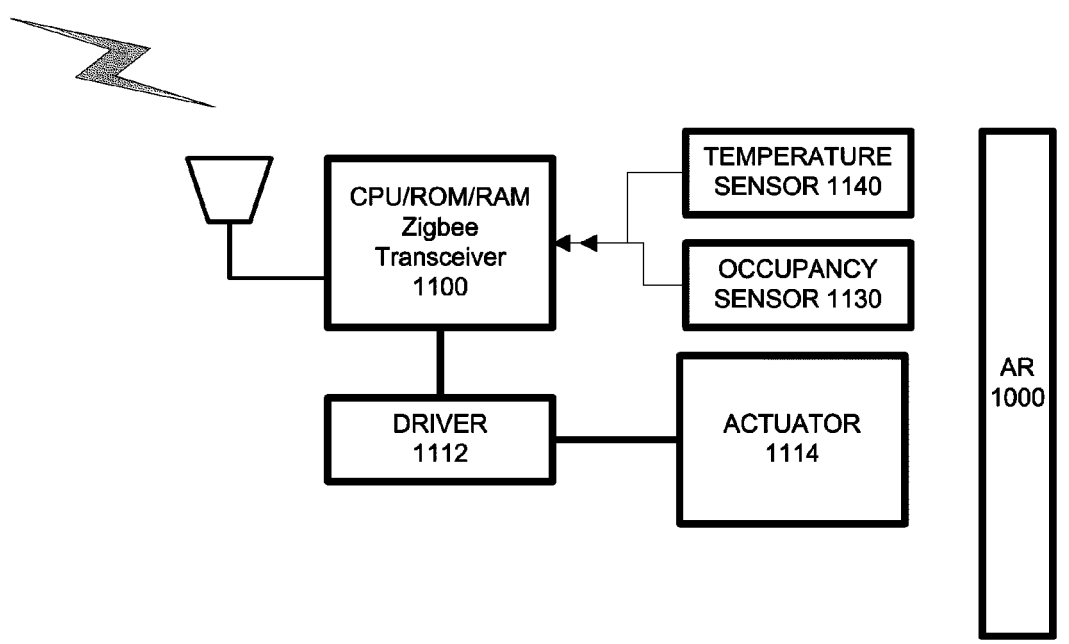

FIG. 12B shows another embodiment similar to FIG. 12A, with the addition of a temperature sensor 1140 and an occupancy sensor 1130. The occupancy sensor 1130 can be a conventional PIR sensor or can be the radar like echo-location described above. In one embodiment, if the occupancy sensor 1130 determines that the room is empty, the vents can be closed to save energy. The temperature sensor 1140 compares room temperature to desired room-temperature and causes the processor to open or close the vent in the air register as desired. A solar cell 111A harvests sunlight and charges the power 1110 which can be a battery or a super-capacitor.

Figure 12C:
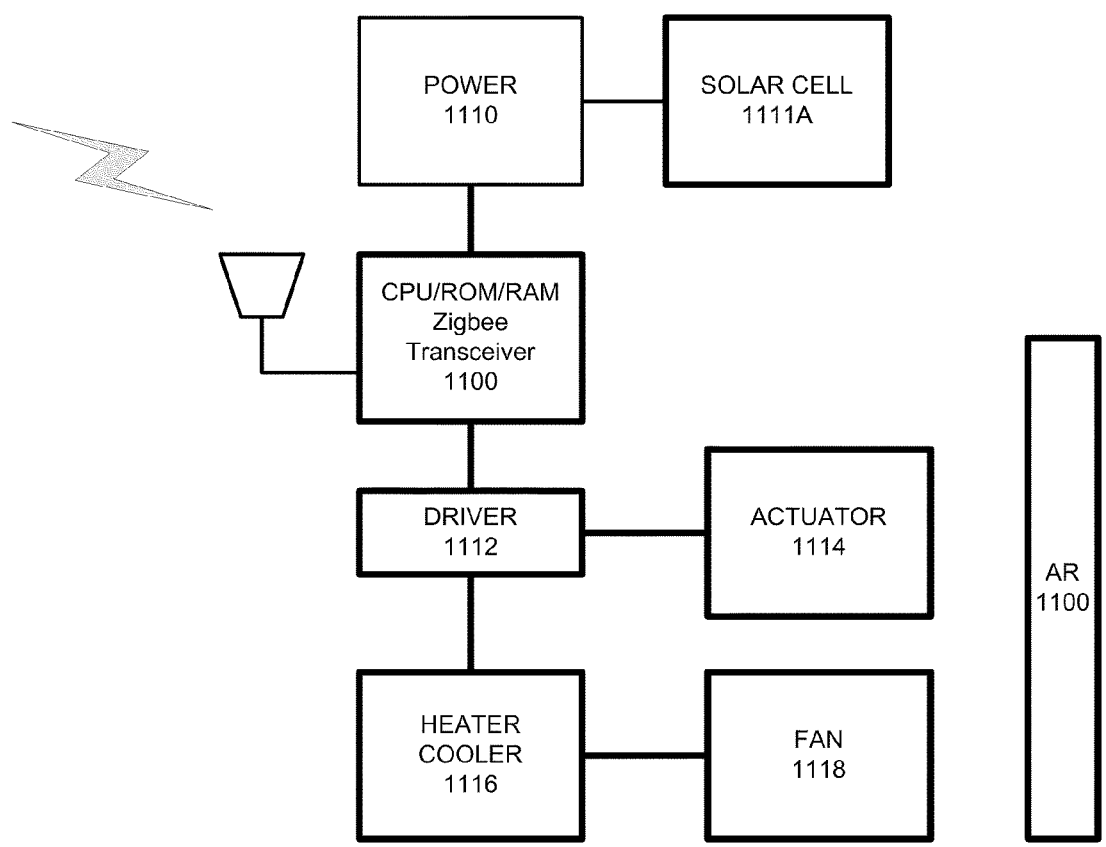
Figure 12D:
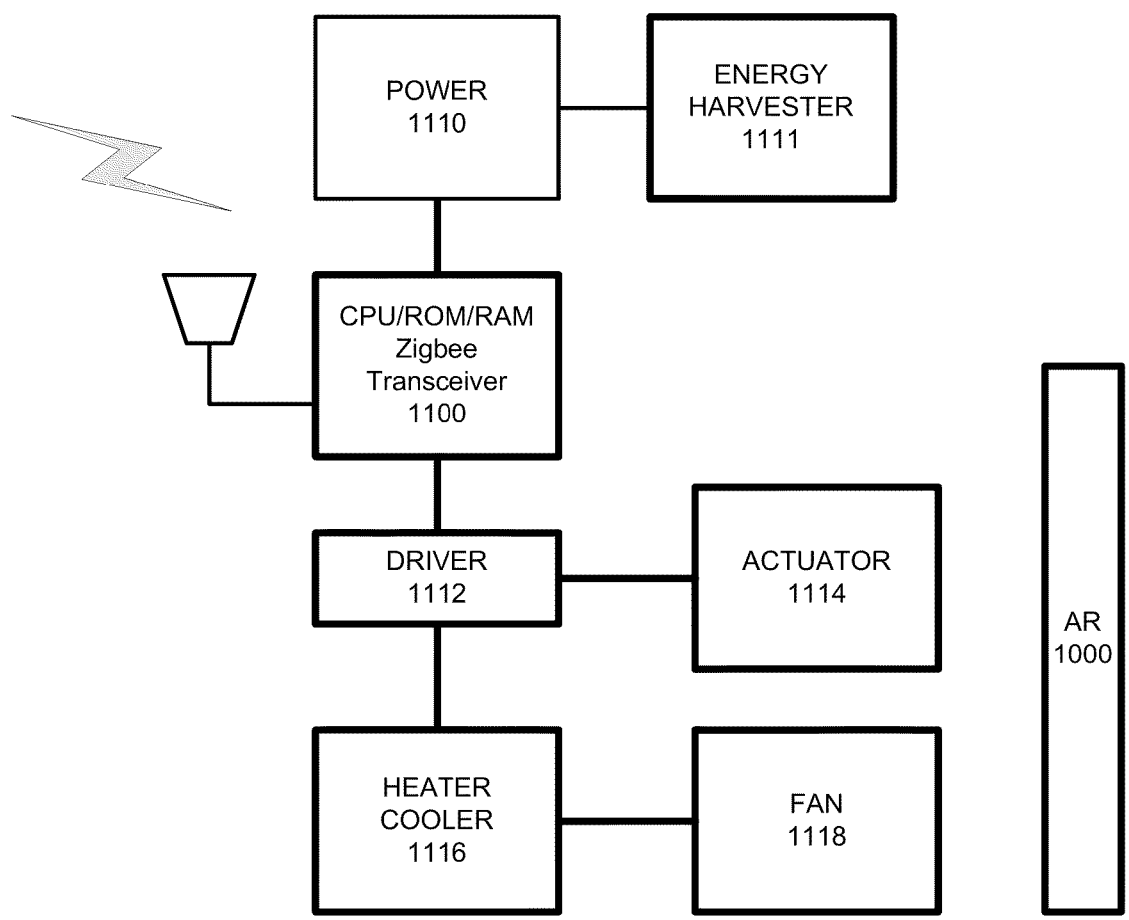

FIG. 12D shows another embodiment where an energy harvester 1111 is used to supply energy to the power 1110. The energy harvester can be piezoelectric that converts vibrations into energy, or can be any other suitable renewable energy source.

Figure 13:
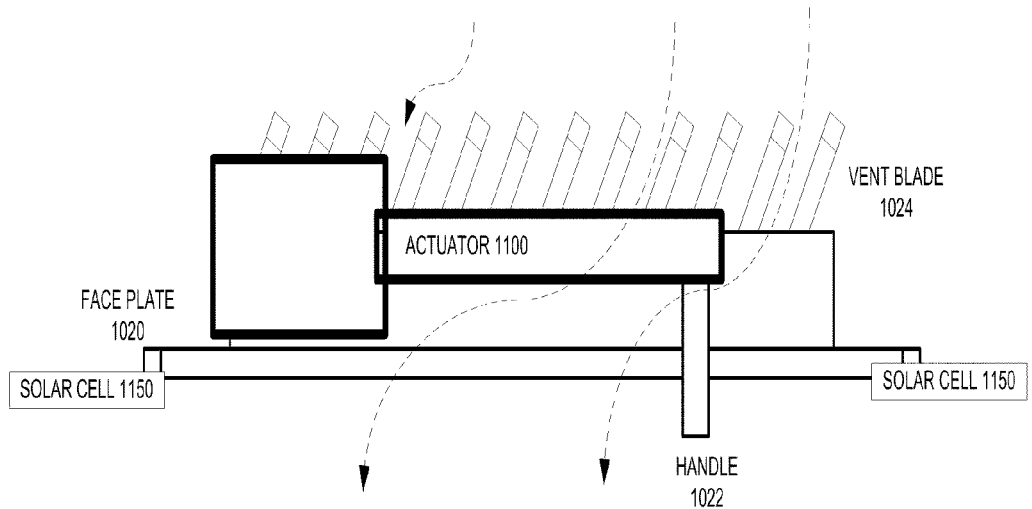
FIG. 13 shows an exemplary solar powered air vent.

FIG. 13 shows an exemplary mounting of solar cells 1150 for the system of FIG. 12C. The solar cells 1150 can be positioned around a face plate 1020 of the air register.

Figure 14:
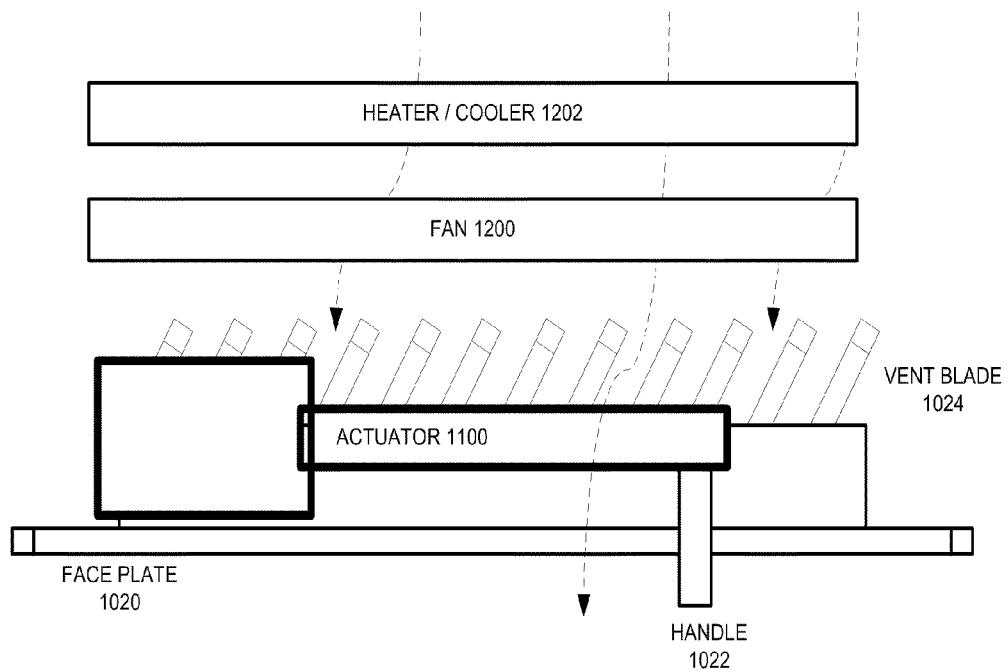
FIG. 14 shows an exemplary air vent with heater/cooler and fan.

FIG. 14 shows an exemplary mounting of heater/cooler 1202 and a fan 1200 above the faceplate 1020.

Figure 15A:
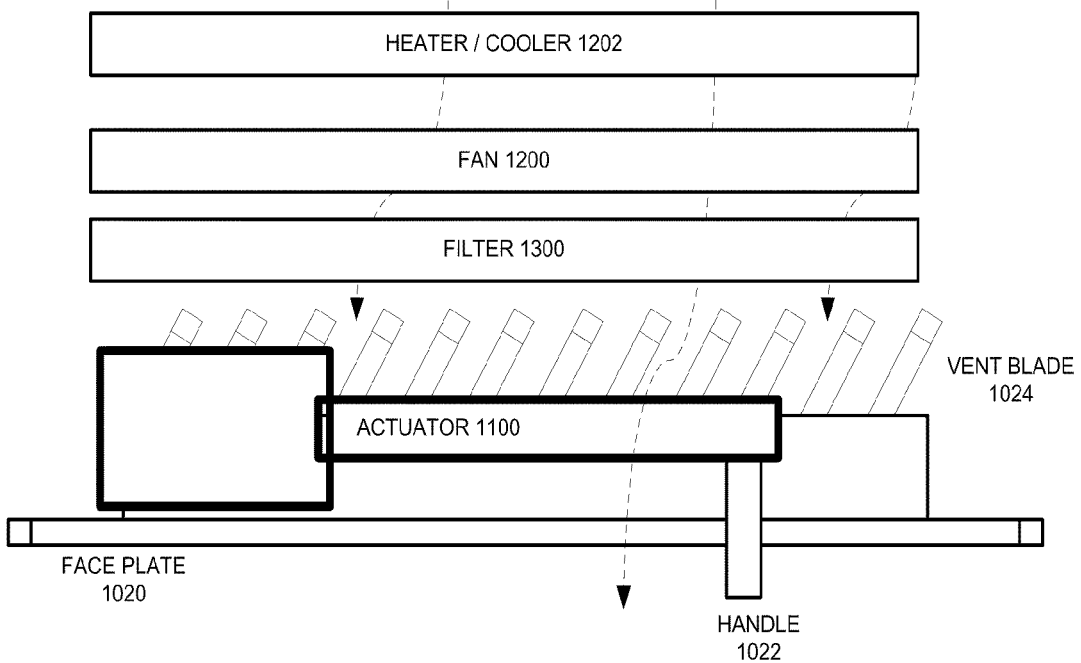
Figure 15B:
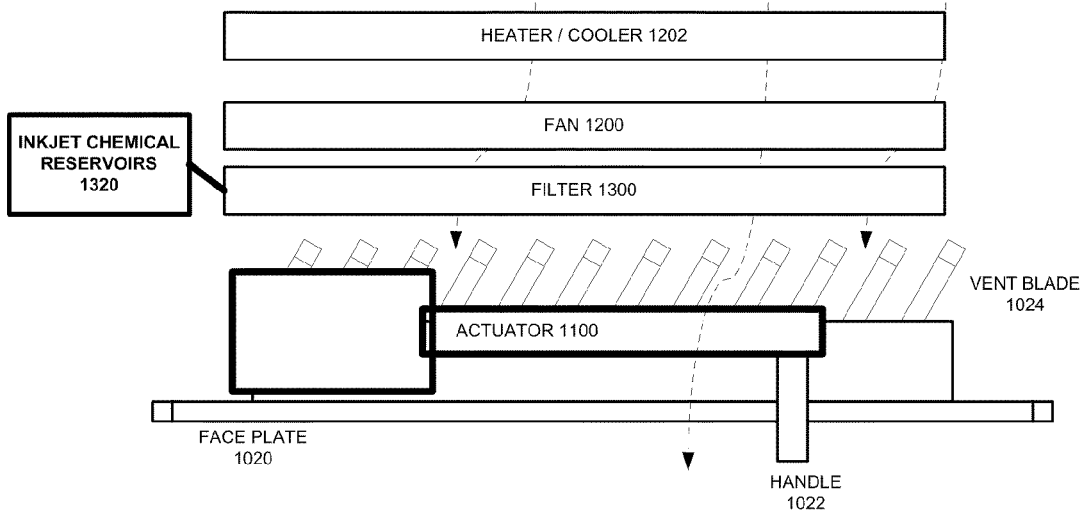
FIG. 15B shows an exemplary air vent with scent control.
Figure 15B:
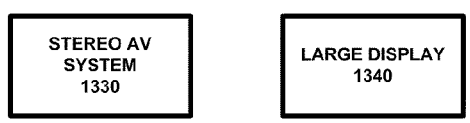

FIG. 15A shows an embodiment with an air filter, while FIG. 15B shows an embodiment where one or more scent reservoirs can be mixed to provide an appropriate scent for a desired room.

The embodiment of FIG. 15A provides supplemental filters 1300 for the duct outlets of a forced air heating system effective to reduce substantially the amount of soot and dirt transmitted from a warm air register into the room. Consumers can select different filter materials to fit individual needs such as pollen and/or odor reduction and to fit the type of heating system used in the individual's home or apartment. The supplemental filter can be changed quickly and easily while minimizing the amount of dust and dirt which can escape the filter during replacement. In this manner, disposable filters impregnated with particular materials, such as activated carbon, remove selected particles or odors, such as cigarette smoke, from the air being transmitted by the forced air duct. Heated or cooled air stream efficiently disperses air freshening scent throughout the room.

FIG. 15B shows another embodiment that provides an air freshening system which can be readily controlled as to type of scent and as to the intensity of a particular type of scent within a room. In this embodiment, one or more electrically actuated chemical reservoirs inject predetermined fragrance(s) into the filter 1300 to provide appropriate scents for the room. In one implementation, the scent(s) can be controlled to match a particular ambience rendered by a stereo system 1330 and a display 1340. Such a system enables an occupant to enjoy a realistic virtual reality immersive presence. For example, the display 1340 can project an HD video loop of an ocean view and the stereo 1330 can play the sound of crashing waves and the chemical reservoirs 1320 can emit a fresh ocean smell that is synchronized with the sound to simulate sea breezes driven by the fan 1200.

The processor can communicate with a remote server for configuration and for reporting usage and controlling the motors. One embodiment uses a cloud-based server system such as the Digi X-Grid system that enables the utility and home owner to accurately manage energy consumption down to an individual home level, providing pre-developed tools that enable the homeowner to view and effectively manage their real-time load information for their HAN. Digi X-Grid solutions allow the utility to remotely manage any diagnostics required of smart meters or devices on the HAN.

Provide real-time access to the HAN
    Enable remote diagnostics of smart meters and other HAN Devices
    Immediately scalable solution
    Easy, out-of-the-box set up In one embodiment, the processor runs the ZigBee Smart Energy Profile, which defines a wireless home area network (HAN) to manage energy in residential areas. These networks are local to the home and connect through a gateway back to a Utility head-end application.

The current devices defined for Smart Energy are:
    Meter—Reports consumption of energy, water, gas, etc.
    Energy Service Interface—Gateway from the Utility head-end to the HAN.
    In-Premise Display—Displays consumption and pricing information for the consumer.
    Programmable Communicating Thermostat (PCT)—Smart thermostat.
    Load Control Device—Can limit or turn off power to devices during high load times.
    Range Extender—Fills in gaps in wireless HAN.

One implementation works with the Digi ConnectPort X2 for Smart Energy, which is a gateway on a Smart Energy network that provides secure access to a ZigBee Smart Energy network over the internet. The gateway is set up to take advantage of connection management services offered by the iDigi platform, and to intelligently handle Smart Energy events in order to reduce the need for communication and micro management by utility applications. The server provides a REST-style API over HTTP (or HTTPS). Users can write HTTP clients in a preferred programming language that get data from the platform and use or display the data in the way that they desire. Examples of such clients include Web pages and programs written in a language such as Python or Java. These clients send requests to the server using standard HTTP requests. The HTTP requests that the iDigi platform supports are GET, PUT, POST, and DELETE. The server supports basic HTTP authentication and only valid users can access the database. To reduce the authentication overhead of multiple requests, either use an HTTP library that caches cookies, or cache the cookies JSESSIONID and SID. Once the data is retrieved from the server, it can be used to do calculations, display graphs, monitor appliances, among others.

A Link Key Database (LKDB) can be used for reducing the complexity of commissioning a Smart Energy ZigBee network requiring the use of a link key without compromising security. The system eliminates the need for a consumer or installer to enter long alpha-numeric strings into an installation user interface, or communicate that data over the phone given that both processes are extremely error prone. The LKDB provides the means for an installation and commissioning application to acquire the necessary link key information to allow requesting ZigBee nodes to join the network upon the approval of the consumer or installer. In this process 1. A customer or installer can login to an installation application which is communicating with the trust center of the ZigBee network (i.e. the coordinator).

2. The customer installs their new Smart Energy device and attempts to join the network.

3. The trust center notifies the installation application that is sees a node attempting to join the network and provides the EUI-64 address of that node.

4. The installation application makes a secure connection to the LKDB, requesting the link key and any other meta-data associated with that EUI.

Assuming the link key had been primed in the LKDB, the installation application prompts the customer or installer with the following information associated with the EUI and any pertinent manufacturer information:

"The following device is attempting to join the ZigBee network (Provide the EUI and manufacturer info). I have the appropriate information to complete the join process, would you like to allow this device on your network?"

This provides a cleaner alternative to requiring the consumer or installer to enter the full EUI-64 and install code into the UI.

One advantage to using the cloud-based energy service is that the Gateway and server work as a cohesive unit. This means that when the server encounters a new Gateway, it discovers all of the Smart Energy devices, clusters and attributes and allows the system to enable reporting at the gateway level for any attributes for which periodic updates are desired. These updates are automatically transmitted to the server from the gateway and stored in the Smart Energy Attribute Data Cache and the system can make requests from your application to retrieve data in a variety of ways:

The system can retrieve data samples at a periodic interval for a single device, list of devices or all devices in an account The system can retrieve historical data samples to retrieve data from the application less frequently The system can request data based on the two previous scenarios for a single device, list of devices or all devices in an account.

"Computer readable media" can be any available media that can be accessed by client/server devices. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by client/server devices. Communication media typically embodies computer readable instructions, data structures, program modules or other data in a modulated data signal such as a carrier wave or other transport mechanism and includes any information delivery media.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only. The above specification, examples and data provide a complete description of the manufacture and use of the composition of the invention. Since many embodiments of the invention can be made without departing from the spirit and scope of the invention, the invention resides in the claims hereinafter appended.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A system to control energy consumption in a building having a plurality of rooms, comprising:
    an occupancy sensor;
    a processor;
    an air register housing the processor and the occupancy sensor, the air register including a motor coupled to the processor and the occupancy sensor, the motor opening or closing one or more air vents in response to sensed motion or room temperature; and
    an air filter proximal to the air register and one or more scent chemical reservoirs coupled to the air filter to dispense computer controlled scent.

2. The system of claim 1, wherein the processor in the air register is wired to the occupancy sensor, wherein the processor reads the output of the occupancy sensor, determines occupancy, and automatically closes the air vent(s) based on user specification or when the room is empty.

3. The system of claim 1, comprising a smart meter coupled to an appliance, wherein the smart meter includes bi-directional communication, power measurement and management capability, software-controllable disconnect switch, and communication over low voltage power line.

4. The system of claim 1, wherein room temperature is controlled by a thermostat or a remote processor sending an instruction to the processor.

5. The system of claim 1, wherein the occupancy sensor comprises a wireless transceiver, wherein the wireless transceiver is periodically used to detect occupancy by detecting variations in reflected radio signals and otherwise used for data communication with another transceiver.

6. The system of claim 1, wherein the processor communicates with an online weather service through an application program interface (API) for predicted weather condition.

7. The system of claim 1, wherein the processor precharges room temperature in response to a demand response signal or a predetermined pattern.

8. The system of claim 1, wherein the processor minimizes operating cost by shifting energy use to an off-peak period in response to utility pricing that varies energy cost by time of day.

9. The system of claim 1, comprising an energy harvester coupled to the processor.

10. The system of claim 9, wherein the energy harvester comprises a solar cell.

11. The system of claim 1, comprising a heating ventilation air conditioning (HVAC) device coupled to a rechargeable energy reservoir, wherein the reservoir is charged during a utility off-peak period and used to power the HVAC device during a utility pricing period.

12. The system of claim 1, comprising a recognizer to determine room usage pattern by occupant(s), wherein the recognizer is coupled to the transceiver including one of: a Hidden Markov Model (HMM) recognizer, a dynamic time warp (DTW) recognizer, a neural network, a fuzzy logic engine, a Bayesian network.

13. The system of claim 1, wherein the occupancy sensor comprises an analyzer to process an RSSI signal from a wireless data transceiver to detect occupancy in the area.

14. The system of claim 1, comprising a light emitting diode coupled to the processor to detect light, wherein the processor determines lighting profiles that incorporate time-based control with occupancy, daylighting, and manual control and wherein the processor integrates time-based lighting control with occupancy sensing control.

15. The system of claim 1, comprising a local heater proximal to the air vent.

16. The system of claim 1, comprising a local air conditioner or cooler proximal to the air vent.

17. The system of claim 1, comprising a local fan proximal to the air vent.

18. The system of claim 1, wherein the occupancy sensor is embedded in the air vent and wherein the occupancy sensor is an infrared occupancy sensor.

19. The system of claim 1, comprising a stereo system and a display to provide an immersive virtual reality experience, through computer controlled scent, sound and video.

\* \* \* \* \*